(12) United States Patent
Takahashi et al.

(10) Patent No.: US 11,261,425 B2
(45) Date of Patent: *Mar. 1, 2022

(54) METHOD FOR INDUCING DIFFERENTIATION OF PLURIPOTENT STEM CELLS INTO NEURAL PRECURSOR CELLS

(71) Applicant: Kyoto University, Kyoto (JP)

(72) Inventors: Jun Takahashi, Kyoto (JP); Asuka Morizane, Kyoto (JP)

(73) Assignee: Kyoto University, Kyoto (JP)

( * ) Notice: Subject to any disclaimer, the term of this patent is extended or adjusted under 35 U.S.C. 154(b) by 400 days.

This patent is subject to a terminal disclaimer.

(21) Appl. No.: 16/141,548

(22) Filed: Sep. 25, 2018

(65) Prior Publication Data

US 2019/0270965 A1   Sep. 5, 2019

Related U.S. Application Data

(63) Continuation-in-part of application No. 13/390,225, filed as application No. PCT/JP2010/063953 on Aug. 12, 2010, now Pat. No. 10,119,120.

(60) Provisional application No. 61/282,970, filed on Apr. 30, 2010, provisional application No. 61/272,055, filed on Aug. 12, 2009.

(51) Int. Cl.
  *C12N 5/0735* (2010.01)
  *C12N 5/074* (2010.01)
  *C12N 5/0793* (2010.01)

(52) U.S. Cl.
  CPC ......... *C12N 5/0606* (2013.01); *C12N 5/0619* (2013.01); *C12N 5/0696* (2013.01); *C12N 2501/15* (2013.01); *C12N 2501/727* (2013.01); *C12N 2501/999* (2013.01); *C12N 2506/02* (2013.01); *C12N 2506/45* (2013.01); *C12N 2533/90* (2013.01)

(58) Field of Classification Search
  CPC ................ C12N 5/0606; C12N 5/0696; C12N 2501/999; C12N 2506/45
  See application file for complete search history.

(56) References Cited

U.S. PATENT DOCUMENTS

| | | |
|---|---|---|
| 2002/0019046 A1 | 2/2002 | Carpenter et al. |
| 2002/0039724 A1 | 4/2002 | Carpenter |
| 2002/0164791 A1 | 11/2002 | Van Der Kooy et al. |
| 2008/0044901 A1 | 2/2008 | Sasai et al. |
| 2010/0009442 A1 | 1/2010 | Sasai et al. |
| 2010/0034785 A1 | 2/2010 | Pedersen et al. |
| 2011/0002897 A1 | 1/2011 | Snyder et al. |
| 2011/0229441 A1 | 9/2011 | Benchoua et al. |
| 2012/0142093 A1* | 6/2012 | Takahashi ............ C12N 5/0618 435/354 |
| 2013/0089870 A1* | 4/2013 | Yamanaka ............ C12N 5/0081 435/7.1 |

FOREIGN PATENT DOCUMENTS

| | | |
|---|---|---|
| EP | 1 783 205 A1 | 5/2007 |
| JP | 2004 533835 | 11/2004 |
| JP | 2008 99662 | 5/2008 |
| WO | WO 02/26941 A2 | 4/2002 |
| WO | 2005 123902 | 12/2005 |
| WO | WO 2008/056166 A2 | 5/2008 |
| WO | WO 2008/056166 A3 | 5/2008 |
| WO | WO 20101063546 A1 | 6/2010 |
| WO | 2010 096496 | 8/2010 |
| WO | 2010 108005 | 9/2010 |
| WO | 2010 108008 | 9/2010 |

OTHER PUBLICATIONS

Chambers et al. Combined small molecule inhibition accelerates developmental timing and converts human pluripotent stem cells into nociceptors. Nat Biotechnol. ; 30(7): 715-720 (Year: 2013).*
Chambers, S.M., et al., "Highly efficient neural conversion of human ES and iPS cells by dual inhibition SMAD signaling," Nature Biotechnology, vol. 27, No. 3, pp. 275-280, (Mar. 2009).
Yu, P.B., et al., "BMP type I receptor inhibition reduces heterotopic ossification," Nature Medicine, vol. 14, No. 12, pp. 1363-1369, (Dec. 2008).
Hao, J., et al., "Dorsomorphin, a Selective Small Molecule Inhibitory of BMP Signaling, Promotes Cardiornyogenesis in Embryonic Stem Cells," PLoS One, vol. 3, No. 8, pp. 1-8, (Aug. 2008).
Tojo, M., et al., "The ALK-5 inhibitor A-83-01 inhibits Smad signaling and epithelial-to-mesenchymal transition by transforming growth factor-β," Cancer Science, vol. 96, No. 11, pp. 791-800, (Nov. 2005).
Smith, J.R., et al., "Inhibition of Activin/Nodal signaling promotes specification of human embryonic stem cells into neuroectoderm," Developmentai Biology, vol. 313, No. 1, pp. 107-117, (2008).
Kim, D.S., et al., "Robust Enhancement of Neural Differentiation from Human ES and iPS Cells Regardiess of their Innate Difference in Differentiation Propensity," Stem Cell Reviews and Reports, vol. 6, No. 2, pp. 270-281, (Apr. 2010).
Honda, M., et al., "A cellular model of Alzheimers' disease produced by genetical modification and neural differentiation of human embryonic stem cel lines," Journal of Clinical and Experimental Medicine, vol. 232, No. 2, pp. 123-127, (Jan. 9, 2010) (with partial English translation).
Wada, T., et al., "Highly Efficient Differentiation and Enrichment of Spinal Motor Neurons Derived from Humans and Monkey Embryonic Stem Cells," PLoS One, vol. 4, No. 8, pp. 1-12 (Aug. 24, 2009).
International Search Report dated Nov. 16, 2010 in PCT/JP10/63953 Filed Aug. 12, 2010.
Claassen et al. ROCK Inhibition Enhances the Recovery and Growth of Cryopreserved Human Embryonic Stem Cells and Human Induced Pluripotent Stem Cells, Mol. Reprod. Dev. 76: 722-732, 2009.

(Continued)

*Primary Examiner* — Taeyoon Kim
(74) *Attorney, Agent, or Firm* — Oblon, McClelland, Maier & Neustadt, L.L.P.

(57) ABSTRACT

The present invention provides a method for inducing differentiation of pluripotent stem cells into neural precursor cells, comprising culturing the pluripotent stem cells in the presence of a small, molecule BMP inhibitor, and induced neural precursor cells prepared by this method.

15 Claims, 19 Drawing Sheets
(11 of 19 Drawing Sheet(s) Filed in Color)

(56) References Cited

OTHER PUBLICATIONS

Office Action dated Jun. 21, 2013, in Singapore Patent Application No. 201200949-4.
Takao Setoguchi, et al., "Treatment of spinal cord injury by transplantation of fetal neural precursor cells engineered to express BMP inhibitor", Experimental Neurology, vol. 189, Sep. 2004, pp. 37-44.
Mitsunori Ota, et al., "BMP and FGF-2 Regulate Neurogenin-2 Expression and the Differentiation of Sensory Neurons and Glia", Developmental Dynamics, vol. 235, No. 3, Mar. 2006, pp. 646-655.
Kiichi Watanabe, et al., "A Rock Inhibitor Permits Survival of Dissociated Human Embryonic Stem Cells", Nature Biotechnology vol. 25 No. 6 Jun. 2007, p. 681-686 (6 pp.).
Extended Search Report dated Aug. 1, 2013 in European Patent Application No. 10808270.2.
Shunmei Chiba, et al., "Noggin Enhances Dopamine Neuron Production from Human Embryonic Stem Cells and Improves Behavioral Outcome After Transplantation into Parkinsonian Rats", Stem Cells, Embryonic Cells/Induced Pluripotent Stem Cells, vol. 26, No. 11, XP055072512, Nov. 1, 2008, pp. 2810-2820.
Ryo Hotta, et al., "Small-Molecule Induction of Neural Crest-like Cells Derived from Human Neural Progenitors", Stem Cells, Embryonic Stem Cells/Induced Pluripotent Stem Cells, XP055072509, Jan. 1, 2009, 10 pages.
Michael F. A. Finley, et al., "BMP-4 Inhibits Neural Differentiation of Murine Embryonic Stem Cells", Journal of Neurobiology, vol. 40, No. 3, XP009017895, Sep. 5, 1999, pp. 271-287.
Martin F. Pera, et al., "Regulation of human embryonic stem cell differentiation by BMP-2 and its antagonist noggin", Journal of Cell Science, vol. 117, No. part 07, XP009030261, Apr. 1, 2004, pp. 1269-1280.
Rickie Patani, et al., "Activin/Nodal Inhibition Alone Accelerates Highly Efficient Neural Conversion from Human Embryonic Stem Cells and Imposes a Caudal Positional Identity", PLoS One, vol. 4, No. 10, XP55072252, Oct. 6, 2009, 7 pages.

\* cited by examiner

A

B

METHOD FOR INDUCING DIFFERENTIATION OF PLURIPOTENT STEM CELLS INTO NEURAL PRECURSOR CELLS

CROSS REFERENCE TO RELATED APPLICATIONS

The present application is a continuation-in-part application of U.S. patent application Ser. No. 13/390,225, filed Feb. 13, 2012, which is a National Stage (371) of PCT/JP2010/063953, filed Aug. 12, 2010, and that claims the priority from U.S. Provisional Patent Application No. 61/272,055, filed Aug. 12, 2009, and No. 61/282,970, filed Apr. 30, 2010.

TECHNICAL FIELD

The present invention relates to a method for inducing the differentiation of pluripotent stem cells into neural precursor cells.

The present invention also relates to induced neural precursor cells prepared by the above method.

BACKGROUND ART

Cells having pluripotency have been reported, such as embryonic stem cells (ES cells) and induced pluripotent stem cells (iPS cells), wherein the iPS cells can be obtained by introducing an undifferentiated cell-specific gene(s) into somatic cells of animals (U.S. Pat. No. 5,843,780 or WO 2007/069666). Hence, one has drawn attention to therapeutic methods comprising transplanting neural cells, which are obtained by differentiation of pluripotent stem cells, which methods may serve as alternative methods for treating neurodegenerative diseases or nerve injuries. The following methods have been developed as methods for inducing the differentiation of ES cells into neural cells: (1) a method for inducing differentiation by causing embryoid body formation in serum free medium (SFEB method) (Watanabe K, et al. Nat Neurosci. 8: 288-96, 2005); (2) a method for inducing differentiation by culturing ES cells on stromal cells (SDIA method) (Kawasaki H, et al. Neuron. 28: 31-40, 2000); and (3) a method for adding a drug onto Matrigel and then culturing (Chambers S M, et al. Nat Biotechnol. 27: 275-80, 2009).

However, there are some problems that undifferentiated cells remain after the induction of the differentiation by these methods, and the use of cytokines in these methods results in very high cost, for example. Accordingly, many small molecule compounds have been developed as cytokine replacements (WO 2008/033408), but which small molecule compounds induce highly efficient differentiation into neural cells remains unknown.

SUMMARY OF INVENTION

An object of the present invention is to provide a highly efficient method for inducing the differentiation of pluripotent stem cells into neural precursor cells using a small molecule compound.

The present invention is characterized as follows.

(1) A method for inducing differentiation of a pluripotent stem cell into a neural precursor cell, comprising culturing the pluripotent stem cell in the presence of a small molecule BMP inhibitor.

(2) The method according to (1), wherein a small molecule TGFβ family inhibitor is further present upon culture.

(3) The method according to (1) or (2), wherein the culture is performed using a stromal cell as a feeder cell.

(4) The method according to (3), wherein the stromal cell is PA6 cell.

(5) The method according to (1) or (2), wherein the culture is performed with formation of an embryoid body under the condition of serum free.

(6) The method according to (1) or (2), wherein the culture is performed on a Matrigel™-coating dish without using feeder cells.

(7) The method according to any one of (1) to (6), wherein the small molecule BMP inhibitor is Dorsomorphin or LDN-193189.

(8) The method according to (2), wherein the small molecule TGFβ family inhibitor is SB431542 or A-83-01.

(9) The method according to any one of (1) to (8), wherein the pluripotent stem cell is an embryonic stem cell or an induced pluripotent stem cell.

(10) The method according to any one of (1) to (9), comprising culturing the pluripotent stem cell in the further presence of ERK (extracellular signal-regulated kinase) inhibitor.

(11) An induced neural precursor cell, which is prepared by the method according to any one of (1) to (10).

According to the above method of the present invention, induced neural precursor cells can be highly efficiently prepared by allowing a small molecule BMP inhibitor to exist in a differentiation induction medium, preferably by allowing the combination of a small molecule BMP inhibitor and a small molecule TGFβ family inhibitor to co-exist in a differentiation induction medium.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A, total number of colonies existing per well on day 14 after differentiation induction in all cell lines (KhES-1, KhES-2, KhES-3, G1, G4, B6, and B7: n=4 for each cell line) (n=28); and FIG. 4B, the ratios (%) of neural cell-containing colonies (positive for Nestin) to undifferentiated cell-containing colonies (positive for Oct3/4) existing per well on day 14 after differentiation induction in all cell lines (KhES-1, KhES-2, KhES-3, G1, G4, B6, and B7: n=4 for each cell line) (n=28). When at least one positive cell could be confirmed within a colony, such colony was counted as a positive colony.

FIG. 9E is a graph showing the number of ES cell-derived cells (black bars), ES cell-derived PSA-NCAM positive cells (white bars), and SSEA4 positive cells (hatch bars) obtained per dish in control group (KhES1 cont) and in differentiation induction group (KhES1+D&SB) for which Dorsomorphin and SB431542 were used. The number of cells was calculated by the following formulae.

(Number of ES cell-derived cells)=(Total cell count in dish)−(Number of PA6 feeder cells in dish)

(Number of ES cell-derived PSA-NCAM positive cells)=(Total cell count in dish)×(Rate of PSA-NCAM positive cells in all cells existing in dish)

(ES cell-derived SSEA4 positive cells)=(Total cell count in dish)×(Rate of SSEA4 positive cells in all cells existing in dish)

FIG. 9F and FIG. 9G show characteristic distribution examples for PA6 cells and ES cell-derived cells (F: PA6 cells alone and G: PA6 cells and KhES1 (cultured in the absence of Dorsomorphin and SB431542)).

Figure 10:
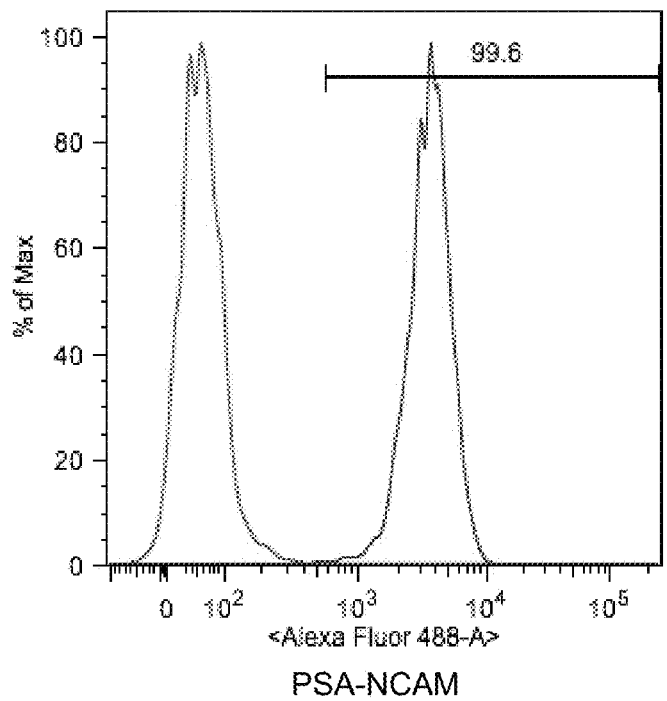
Figure 10:
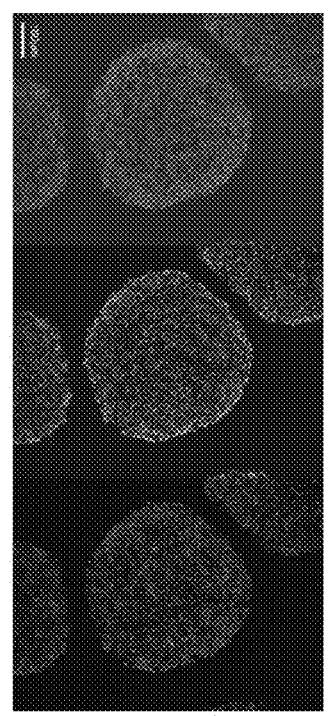

FIG. 10A is a graph showing the percentage of PSA-NCAM positive cells on day 14 after induction of the differentiation of iPS cells (G4) by forming an embryoid body from the iPS cells without feeder cells, followed by culturing the cells in a medium supplemented with Dorsomorphin and SB431542. Here, the red curve indicates the result for a negative control in which no antibody was present and the blue curve indicates the result for cells stained with an anti-PSA-NCAM antibody. Also, FIG. 10B is immunostaining images for Nestin (green) and Pax6 (red) for which the differentiation was induced by the above method.

Figure 11:
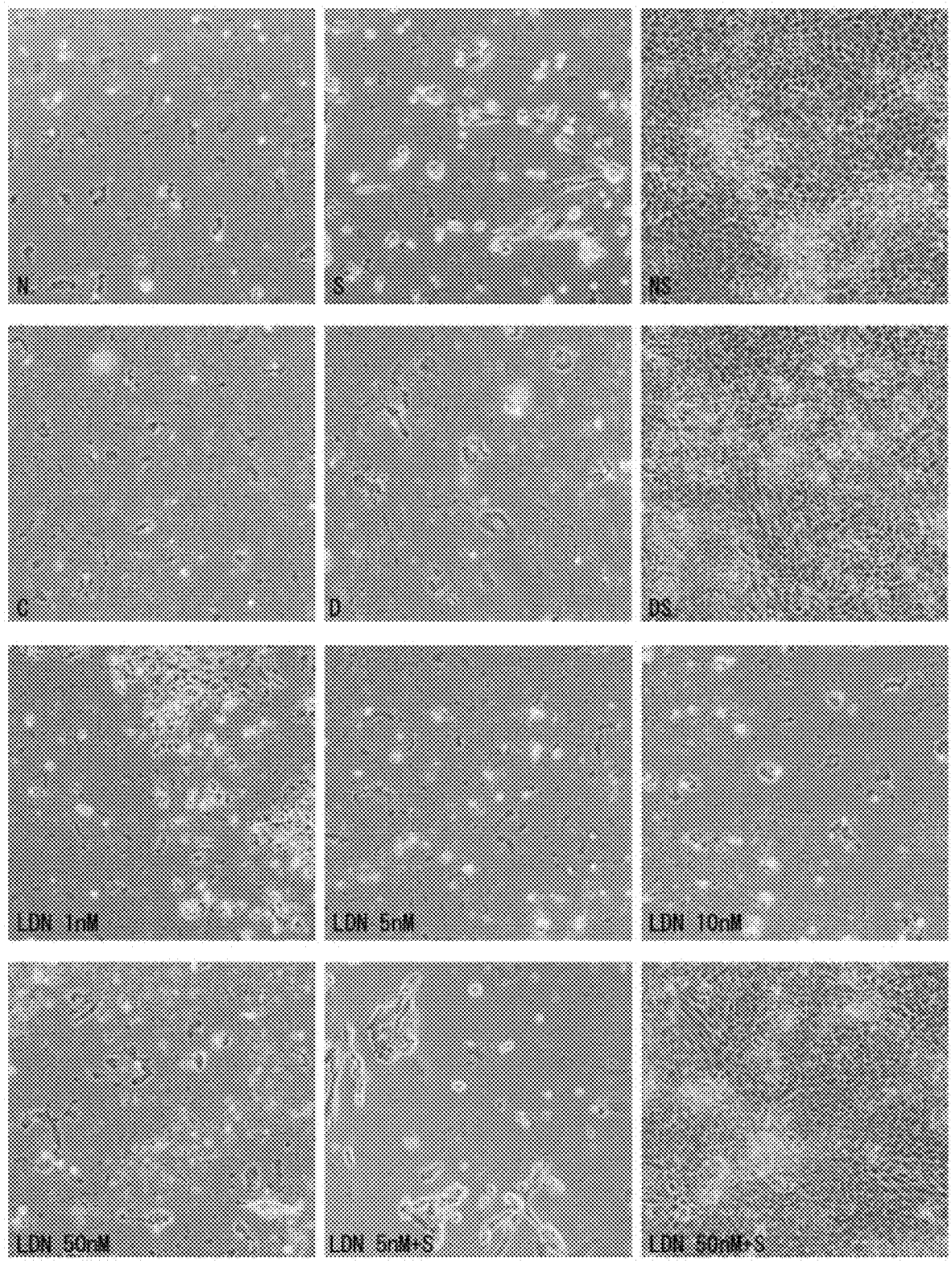

FIG. 11 shows phase contrast microscopic images on day 14 after induction of the differentiation of iPS cells (G4) by culturing the iPS cells without feeder cells by the Matrigel method in a medium supplemented with each of the following drugs. In this figure, "N" indicates addition of Noggin, "S" indicates addition of SB431542, "NS" indicates addition of Noggin and SB431542, "C" indicates addition of control DMSO, "D" indicates addition of Dorsomorphin, "DS" indicates addition of Dorsomorphin and SB431542, "LDN" indicates addition of LDN-193189, and "LDN+S" indicates addition of LDN-193189 and SB431542.

Figure 12:
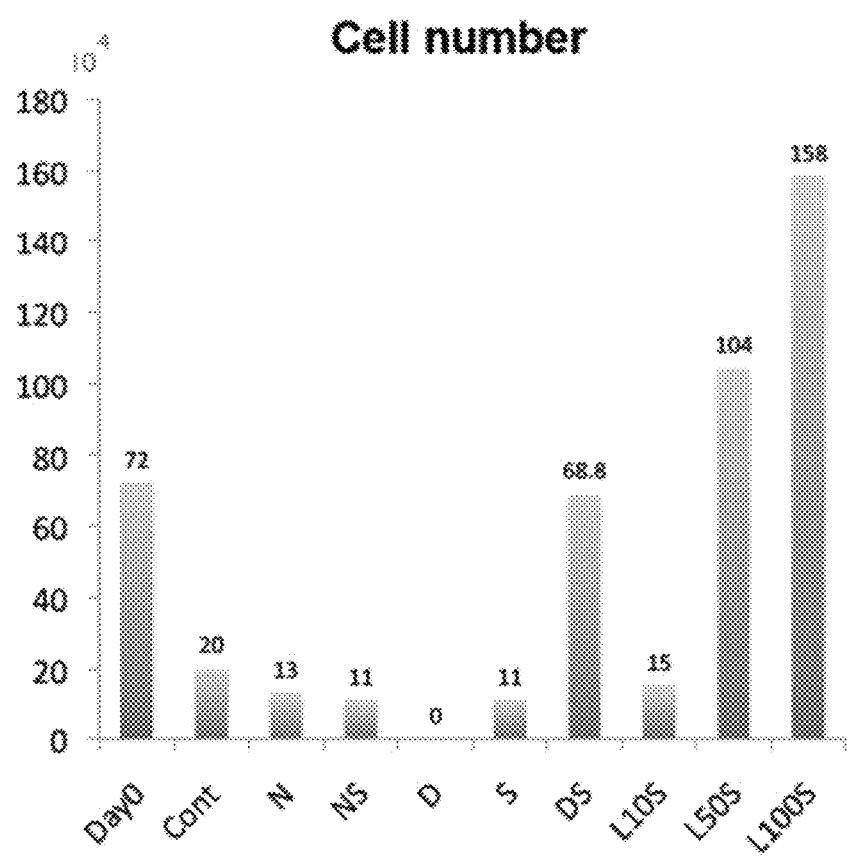

FIG. 12 shows the number of cells (or cell number) existing per well on day 14 after addition of each of the following drugs and the same before addition of each drug. In this figure, Day 0 indicates "before addition of a drug," "Cont" indicates a control group to which DMSO was added, "N" indicates a group to which Noggin was added, "NS" indicates a group to which Noggin and SB431542 were added, "D" indicates a group to which Dorsomorphin was added, "S" indicates a group to which SB431542 was added, "DS" indicates a group to which Dorsomorphin and SB431542 were added, "L10S" indicates a group to which 10 nM LDN-193189 and SB431542 were added, "L50S" indicates a group to which 50 nM LDN-193189 and SB431542 were added, and "L100S" indicates a group to which 100 nM LDN-193189 and SB431542 were added.

Figure 13:
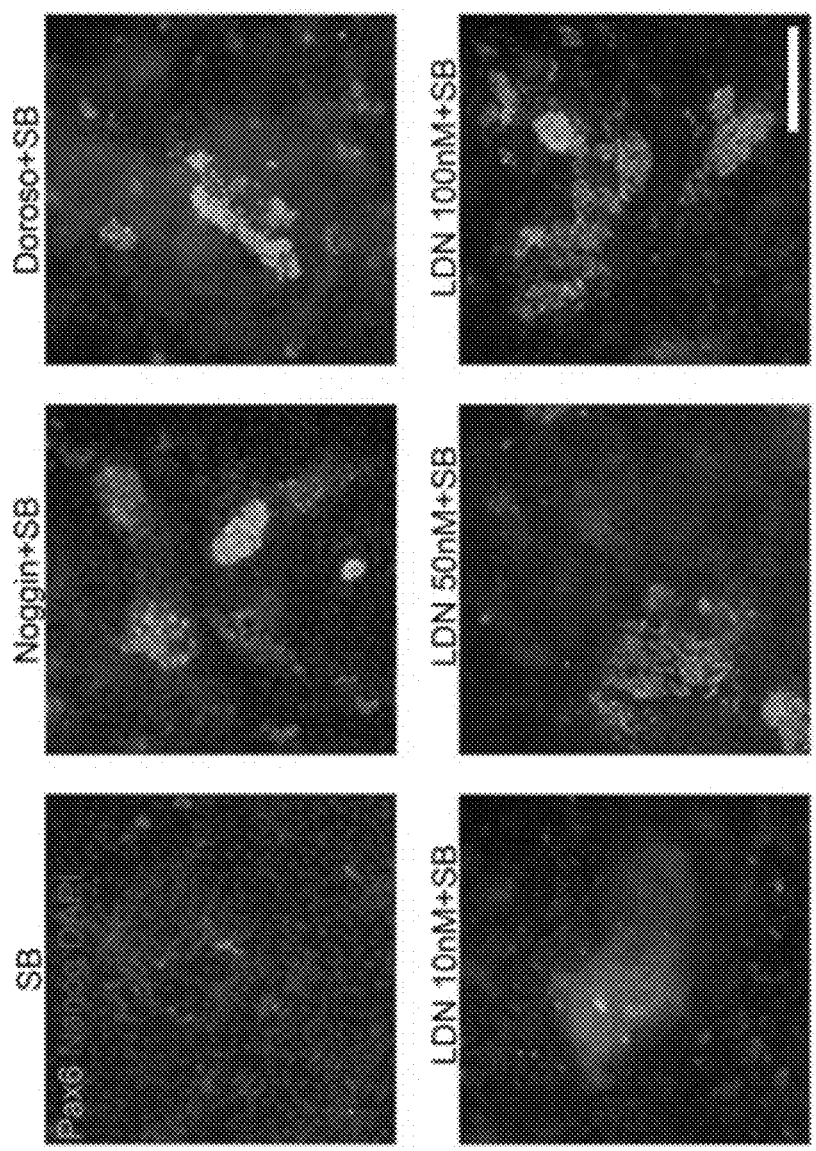

FIG. 13 shows immunostaining images obtained using anti-Pax6 antibody (green) and anti-Nanog antibody (red) and immunostaining images obtained using DAPI (blue) on day 14 after the differentiation of iPS cells (G4) was induced by culturing the cells without feeder cells by the Matrigel method. In FIG. 13, "SB" indicates SB431542 and "LDN" indicates LDN-193189.

Figure 14A:
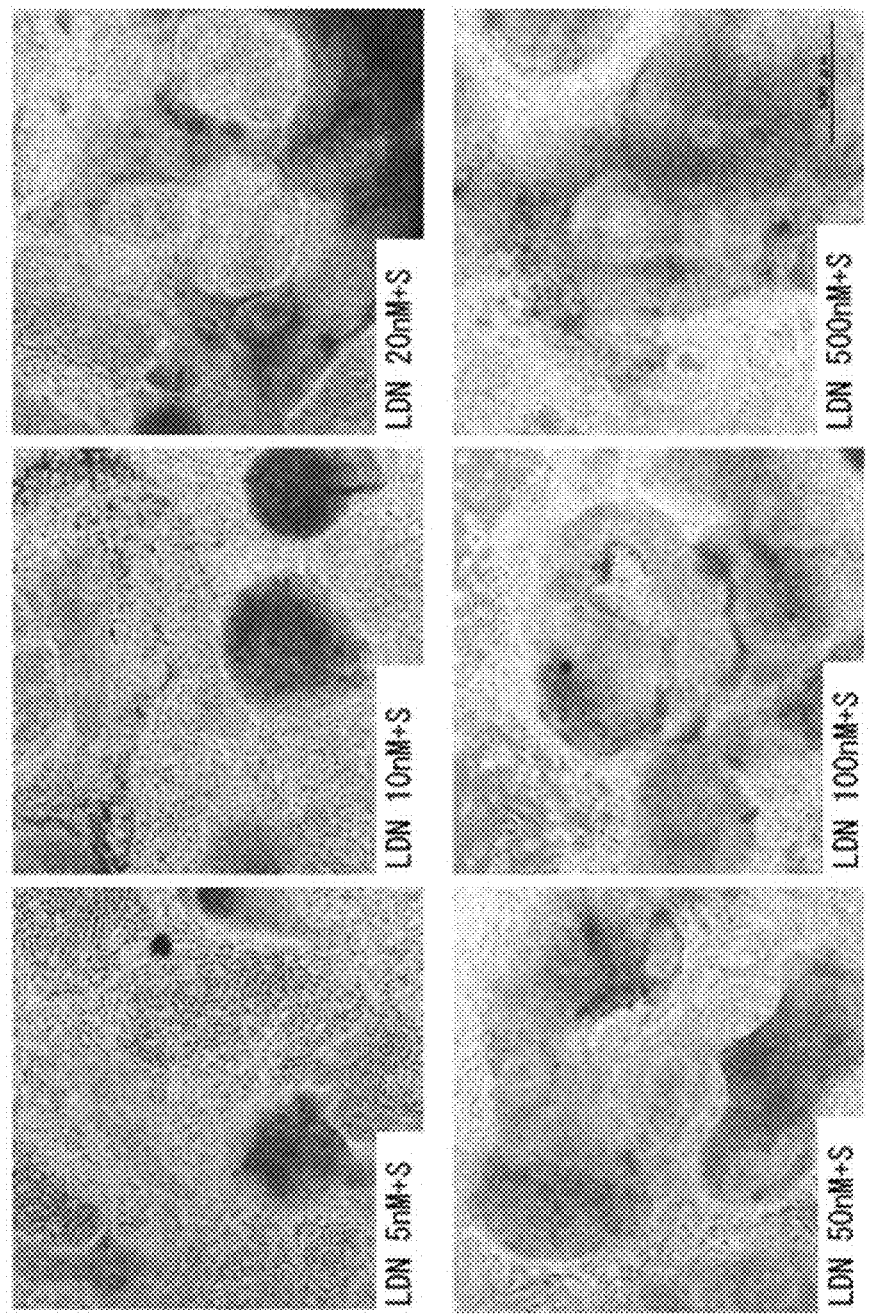
Figure 14B:
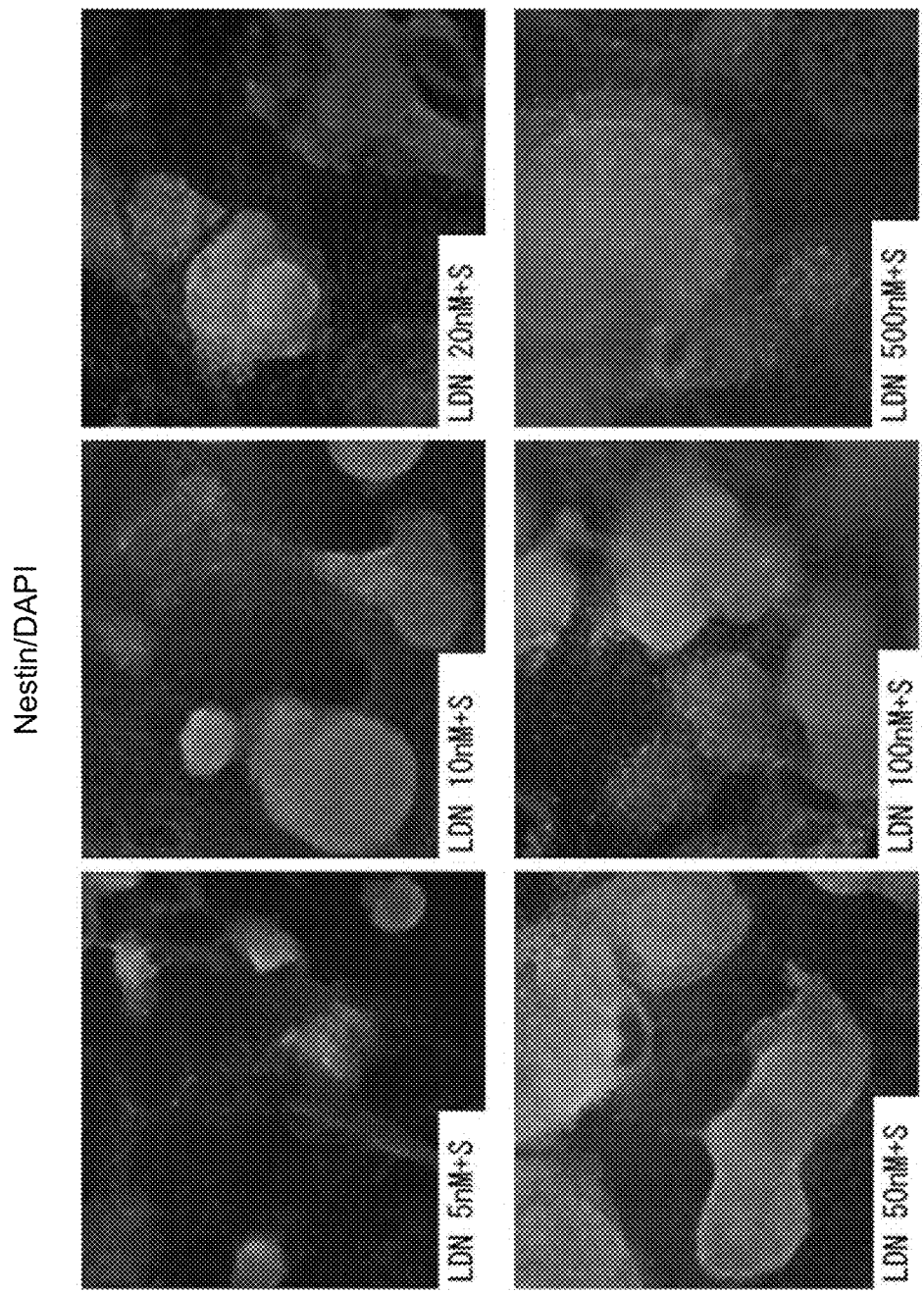

FIG. 14 shows phase contrast microscopic images (FIG. 14A) and immunostaining images (FIG. 14B) obtained using anti-Nestin antibody (green) and DAPI (blue), on day 14 after differentiation induction. Differentiation was induced by co-culturing an ES cell line (Kh-ES5) with PA6 cells according to the SDIA method, then culturing the cells in a medium supplemented with 5-500 nM LDN-193189 and SB431542.

Figure 15A:
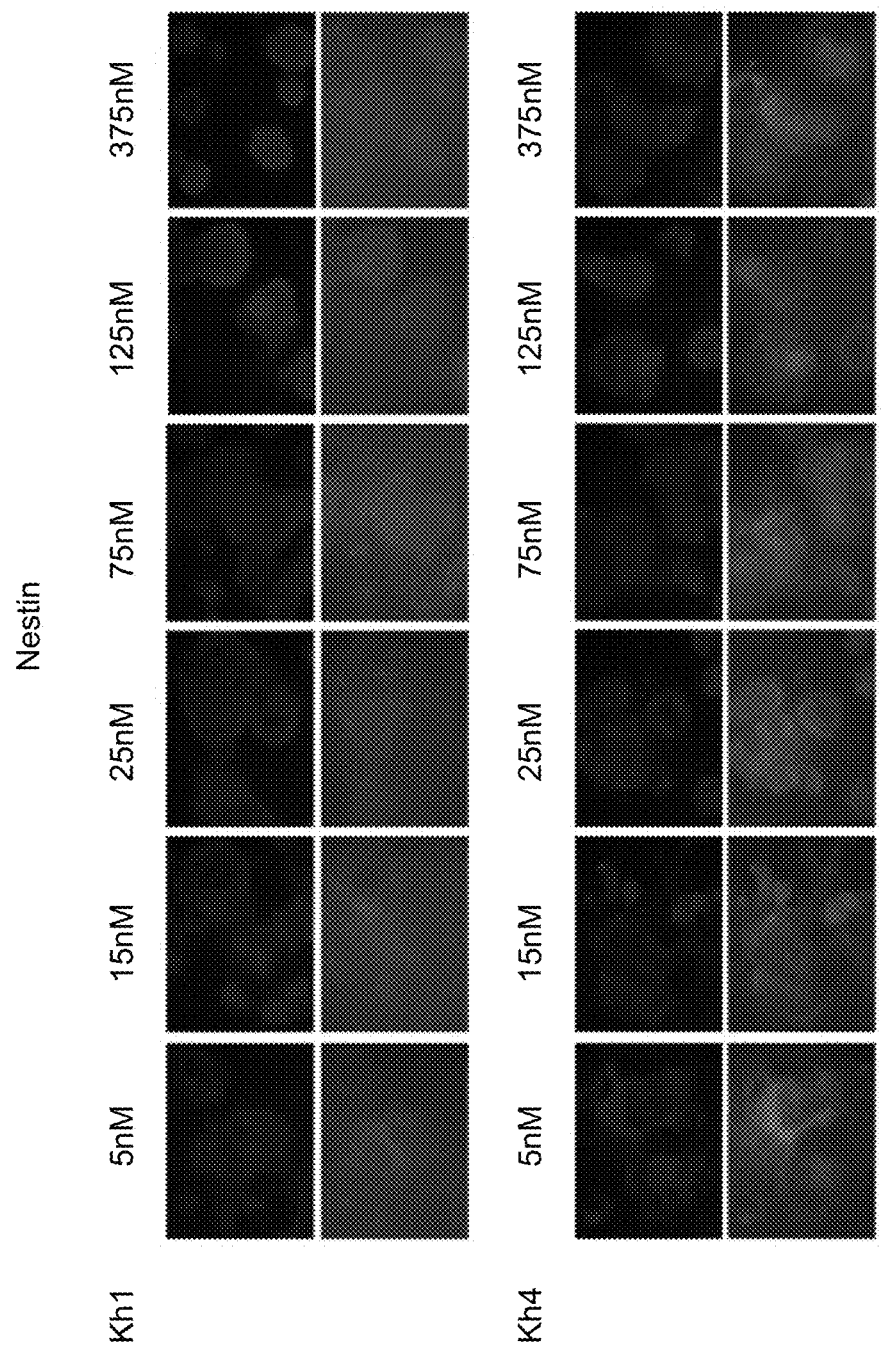
Figure 15B:
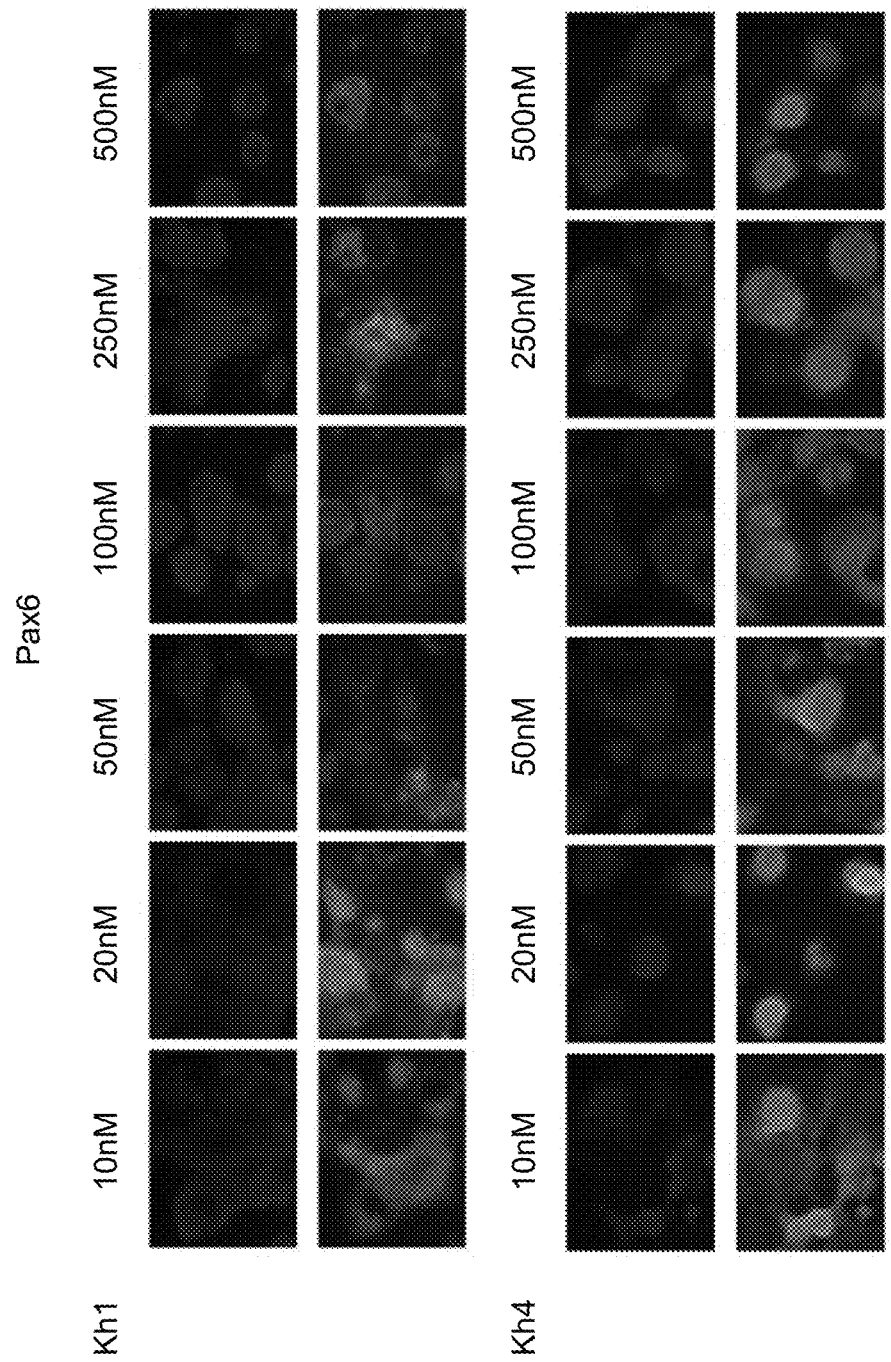

FIG. 15 shows immunostaining images obtained using DAPI (blue) and anti-Nestin antibody (green) (FIG. 15A) or anti-Pax6 antibody (green) (FIG. 15B), on day 14 after induction of differentiation by co-culturing ES cell lines (Kh-ES1 or Kh-ES4) with PA6 cells according to the SDIA method and then culturing the cells in a medium supplemented with 5-500 nM LDN-193189 and SB431542.

Figure 16:
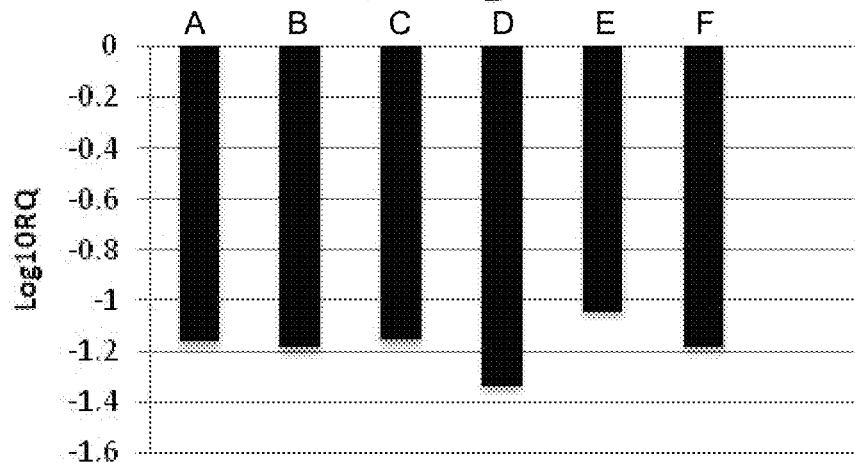
Figure 16:
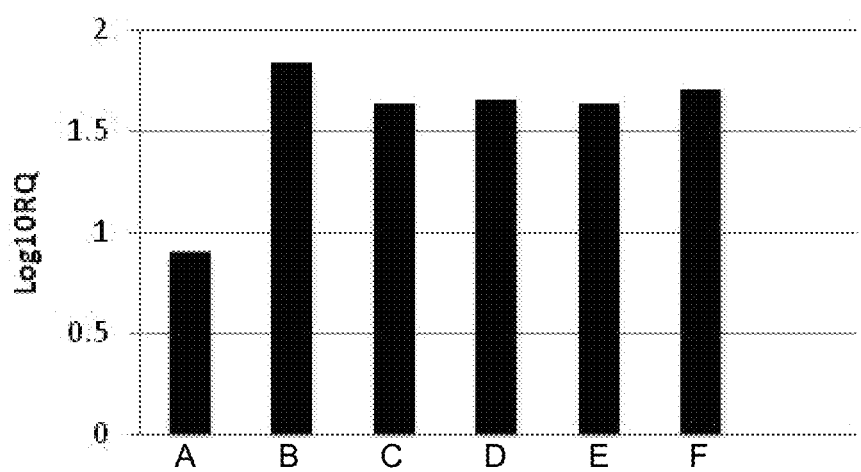
Figure 16:
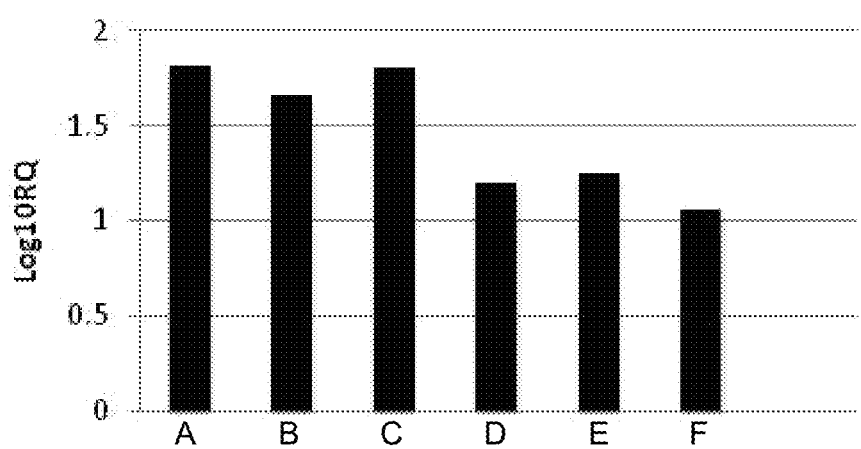

FIG. 16 shows the result of quantitative-PCR with respect to Nanog (FIG. 16A), Pax6 (FIG. 16B) and Sox1 (FIG. 16C) in the differentiated cells induced by culturing human iPS cells (404C2) with feeder-free method. The result shows relative logarithmic value for the value of untreated cells. "A" to "F" indicates the following conditions: "A" is old DFK5% containing 2 μM Dorsomorphin and 10 μM SB431542; "B" is old GMK8% containing 100 nM LDN913189 and 0.5 μM A-83-01; "C" is DFK5% containing 2 μM Dorsomorphin and 10 μM SB431542; "D" is GMK8% containing 100 nM LDN913189 and 0.5 μM A-83-01; "E" is GMK8% containing 100 nM LDN913189 and 10 μM SB431542; and "F" is GMK8% containing 100 nM LDN913189 and 0.5 μM A-83-01+0.5 μM PD0325901.

Figure 17:
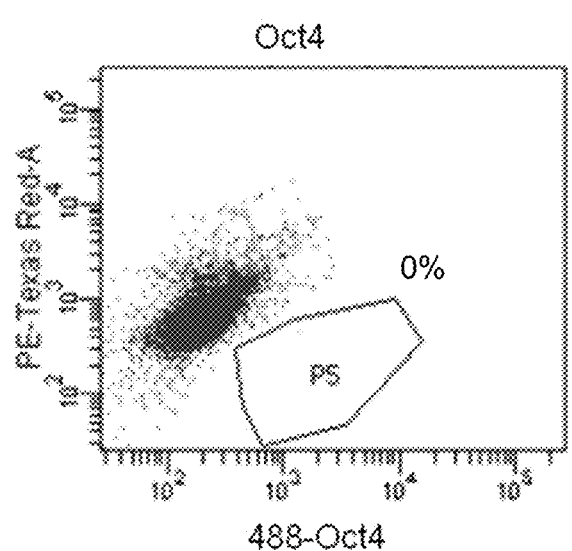
Figure 17:
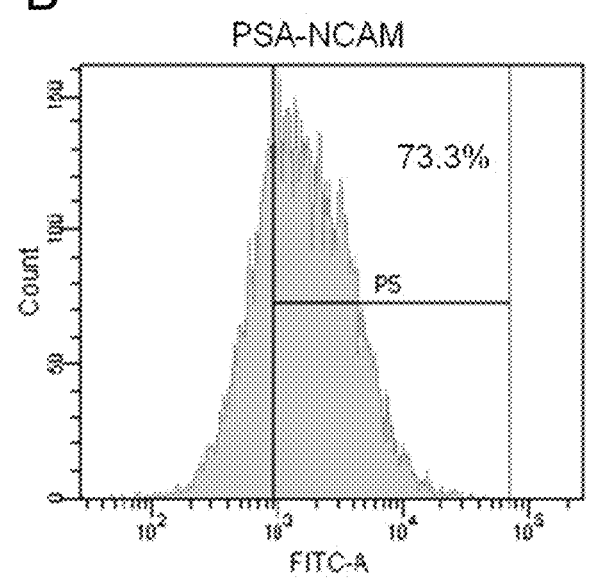
Figure 17:
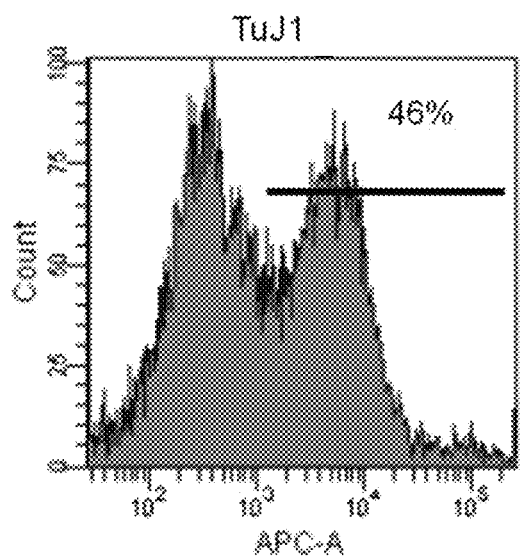
Figure 17:
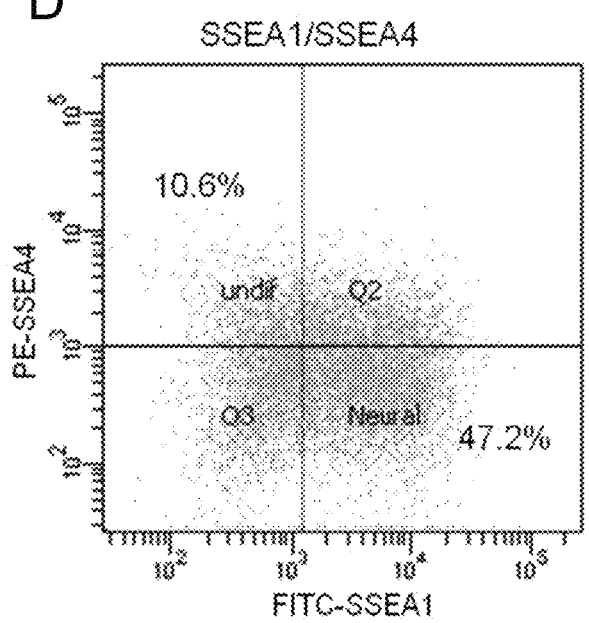

FIG. 17 shows FACS graphs showing 2D-deployment of Oct3/4 (FIG. 17A), PSA-NCAM-expressing cells (FIG. 17B), Tuj-1-expressing cells (FIG. 17C) and 2D-deployment of SSEA1 and SSEA4 (FIG. 17D) with respect to the differentiated cells by culturing iPS cells (404C2) using feeder-free method under the condition of GMK8% containing 100 nM LDN913189 and 0.5 μM A-83-01.

MODES FOR CARRYING OUT THE INVENTION

The present invention will be described in detail as follows.

The present invention relates to a method for inducing differentiation of a pluripotent stem cell into a neural precursor cell, comprising culturing the pluripotent stem cell in the presence of a small molecule BMP inhibitor, as described above.

<Pluripotent Stem Cells>

Pluripotent stem cells that can be used in the present invention are stem cells having the pluripotency which is an ability to differentiate the stem cells into all cells derived from ectoderm, mesoderm and endoderm existing in a living body, and the proliferation potency. Examples of such stem cells include, but are not limited to, embryonic stem (ES) cells, embryo clone-derived embryonic stem (ntES: nuclear transfer ES) cells obtained via nuclear transplantation, male germline stem cells ("GS cells"), embryonic germ cells ("EG cells"), and induced pluripotent stem (iPS) cells. Preferable pluripotent stem cells are ES cells, ntES cells, and iPS cells.

(A) Embryonic Stem Cells

ES cells are stem cells having pluripotency and proliferation potency based on self-replication, which are established from inner cell masses of early embryos (e.g., blastocysts) of mammals such as humans and mice.

ES cells are embryo-derived stem cells from the inner cell masses of the blastocysts that are embryos after the morula stage at the 8-cell stage of fertilized egg. ES cells have namely, pluripotency, which is the ability to differentiate into any cells composing an adult body, and the existence of proliferation potency based on self-replication. ES cells were discovered in mice in 1981 (M. J. Evans and M. H. Kaufman (1981), Nature 292: 154-156) and then ES cell lines were established for primates such as humans and monkeys (J. A. Thomson et al. (1999), Science 282: 1145-1147; J. A. Thomson et al. (1995), Proc. Natl. Acad. Sci. U.S.A., 92: 7844-7848; J. A. Thomson et al. (1996), Biol. Reprod., 55: 254-259; J. A. Thomson and V. S. Marshall (1998), Curr. Top. Dev. Biol., 38: 133-165).

ES cells can be established by removing inner cell masses from blastocysts of fertilized eggs of a target animal, culturing the inner cell masses on fibroblasts as feeder cells. Also, cell maintenance by subculture can be performed using a medium supplemented with a substance such as a leukemia inhibitory factor (LIF) or a basic fibroblast growth factor (bFGF). Methods for establishment and maintenance of human and monkey ES cells are described in H. Suemori et al. (2006), Biochem. Biophys. Res. Commun., 345: 926-932; M. Ueno et al. (2006), Proc. Natl. Acad. Sci. U.S.A., 103: 9554-9559; H. Suemori et al. (2001), Dev. Dyn., 222:273-279; H. Kawasaki et al. (2002), Proc. Natl. Acad. Sci. U.S.A., 99: 1580-1585, etc.

As a medium for preparation of ES cells, a DMEM/F-12 medium supplemented with 0.1 mM 2-mercaptoethanol, 0.1 mM nonessential amino acids, 2 mM L-glutamate, 20% KSR and 4 ng/ml β-FGF is used, for example. Human ES cells can be maintained using the medium under wet atmosphere (5% $CO_2$) at 37° C. Also, ES cells require subculture every 4 to 5 days. At this time, subculture can be performed using 0.25% trypsin and 0.1 mg/ml collagenase IV in PBS containing 1 mM $CaCl_2$ and 20% KSR, for example.

ES cells can be generally selected by the Real-Time PCR method using the expression of a gene marker (e.g., alkaline phosphatase, Oct-3/4, and Nanog) as an indicator. In particular, human ES cells can be selected using the expression of a gene marker (e.g., OCT-3/4, NANOG, or ECAD) as an index (E. Kroon et al. (2008), Nat. Biotechnol., 26: 443-452). Human ES cell lines, such as KhES-1, KhES-2, KhES-3, KhES-4, and KhES-5 are available at the Institute for Frontier Medical Sciences, Kyoto University (Kyoto, Japan).

(B) Male Germline Stem Cells

Male germline stem cells are testis-derived pluripotent stem cells, which serve as origins for spermatogenesis. The cells can be induced to differentiate into various lines of cells as in the case of ES cells. For example, the cells are capable of producing chimeric mice when transplanted in mouse blastocysts (M. Kanatsu-Shinohara et al. (2003) Biol. Reprod., 69:612-616; K. Shinohara et al. (2004), Cell, 119:1001-1012). The cells are self-replicable in a medium containing a glial cell line-derived neurotrophic factor (GDNF). Moreover, through repetition of subculture of the cells under culture conditions similar to those for ES cells, male germline stem cells can be obtained (Masanori Takebayashi et al., (2008), Experimental Medicine, Vol. 26, No. 5 (Suppl.), pp. 41-46, YODOSHA (Tokyo, Japan)).

(C) Embryonic Germ Cells

Embryonic germ cells are established from primordial germ cells at the prenatal period, having pluripotency similar to that of ES cells. Embryonic germ cells can be established by culturing primordial germ cells in the presence of a substance such as LIF, bFGF, and a stem cell factor (Y. Matsui et al. (1992), Cell, 70: 841-847; J. L. Resnick et al. (1992), Nature, 359: 550-551).

(D) Induced Pluripotent Stem Cells

Induced pluripotent stem (iPS) cells can be prepared by introducing a specific reprogramming factor(s) in the form of DNA or protein into somatic cells. Such iPS cells are artificial stem cells from somatic cells, having properties almost equivalent to those of ES cells, such as pluripotency and proliferation potency based on self-replication (K. Takahashi and S. Yamanaka (2006) Cell, 126: 663-676; K. Takahashi et al. (2007), Cell, 131: 861-872; J. Yu et al. (2007), Science, 318: 1917-1920; Nakagawa, M. et al., Nat. Biotechnol. 26: 101-106 (2008); international publication WO 2007/069666). A reprogramming factor may be a gene that is expressed specifically in ES cells or a gene or a gene product thereof playing an important role in maintenance of undifferentiation of ES cells. Examples of such reprogramming factor include, but are not particularly limited to, combinations of: OCT3/4, SOX2 and KLF4; OCT3/4, KLF4 and C-MYC; OCT3/4, SOX2, KLF4 and C-MYC; OCT3/4 and SOX2; OCT3/4, SOX2 and NANOG; OCT3/4, SOX2 and LIN28; and OCT3/4 and KLF4.

These factors in the form of protein may be introduced into somatic cells by techniques such as lipofection, binding with a cell membrane-permeable peptide, and microinjection. Alternatively, these factors in the form of DNA may also be introduced into somatic cells by techniques such as techniques using vectors such as a virus, a plasmid, and an artificial chromosome, lipofection, techniques using liposomes, and microinjection. Examples of a viral vector include a retroviral vector, a lentiviral vector (Cell, 126, pp. 663-676, 2006; Cell, 131, pp. 861-872, 2007; Science, 318, pp. 1917-1920, 2007), an adenoviral vector (Science, 322, pp. 945-949, 2008), and an adeno-associated viral vector, and a Sendai virus vector. Also, examples of an artificial chromosome vector include a human artificial chromosome (HAC), a yeast artificial chromosome (YAC), and a bacterial artificial chromosome (BAC, PAC) vectors. As plasmids, plasmids for mammalian cells can be used (Science, 322: 949-953, 2008). A vector can comprise regulatory sequences such as a promoter, an enhancer, a ribosome binding sequence, a terminator, and a polyadenylation site, so that the nuclear reprogramming factors can be expressed. A vector can further comprise, if necessary, a selection marker sequence such as a drug resistance gene (e.g., kanamycin resistance gene, ampicillin resistance gene, or puromycin resistance gene), a thymidine kinase gene, and a diphtheria toxin gene, a reporter gene sequence such as a green fluorescent protein (GFP), β glucuronidase (GUS), or FLAG. Also, the vector may have LoxP sequences, which are located at each end of a gene encoding a reprogramming factor or a gene encoding a reprogramming factor that binds to the promoter after introduction into somatic cells, in order to cut out the gene.

To increase an induction efficiency upon reprogramming, in addition to the above factors, histone deacetylase (HDAC) inhibitors [e.g., small molecule inhibitors such as valproic acid (VPA) (Nat. Biotechnol., 26 (7): 795-797 (2008)), trichostatin A, sodium butyrate, MC 1293, and M344; siRNA and shRNA against HDAC (e.g., nucleic acid expression inhibitors such as HDAC1 siRNA Smartpool™ (Millipore) and HuSH 29mer shRNA Constructs against HDAC1 (OriGene))], DNA methyltransferase inhibitors (e.g., 5'-azacytidine) (Nat. Biotechnol., 26 (7): 795-797 (2008)), G9a histone methyltransferase inhibitors [e.g., small molecule inhibitors such as BIX-01294 (Cell Stem Cell, 2: 525-528 (2008)) and nucleic acid expression inhibitors such as siRNA and shRNA against G9a (e.g., G9a siRNA (human) (Santa Cruz Biotechnology))], L-channel calcium agonists (e.g., Bayk 8644) (Cell Stem Cell, 3, 568-574 (2008)), p53 inhibitors (e.g., siRNA and shRNA against p53 (Cell Stem Cell, 3, 475-479 (2008)), UTF1 (Cell Stem Cell, 3, 475-479 (2008)), Wnt Signaling (e.g., soluble Wnt3a) (Cell Stem Cell, 3, 132-135 (2008)), 2i/LIF ("2i" indicates a mitogen-activated protein kinase signaling and glycogen synthase kinase-3 inhibitor, PloS Biology, 6 (10), 2237-2247 (2008)), miRNA such as miR-291-3p, miR-294, and miR-295 (R. L. Judson et al., Nat. Biotech., 27:459-461) (2009), ALKS inhibitors (e.g., SB431542), and the like can be used.

Examples of a culture medium for iPS cell induction include (1) a 10%-15% FBS-containing DMEM, DMEM/F12, or DME medium (these media may further appropriately contain LIF, penicillin/streptomycin, puromycin, L-glutamine, nonessential amino acids, β-mercaptoethanol, and the like) and (2) a bFGF- or SCF-containing medium for ES cell culture, such as a medium for mouse ES cell culture (e.g., a TX-WES medium, Thromb-X) or a medium for primate ES cell culture (e.g., a medium for primate (human and monkey) ES cell culture, ReproCELL, Kyoto, Japan).

An example of culture methods is as follows. Somatic cells are brought into contact with reprogramming factors (DNA or protein) on a DMEM or DMEM/F12 medium containing 10% FBS at 37° C. in the presence of 5% $CO_2$ and then cultured for about 4 to 7 days. Subsequently, the cells are reseeded on feeder cells (e.g., mitomycin C-treated STO cells or SNL cells). About 10 days after contact between the somatic cells and the reprogramming factors, cells are cultured in a bFGF-containing medium for primate ES cell culture. About 30-45 days or more after the contact, iPS cell-like colonies can be formed.

Alternatively, cells may be cultured on feeder cells (e.g., mitomycin C-treated STO cells or SNL cells) at 37° C. in the presence of 5% $CO_2$ in a 10% FBS-containing DMEM medium (the medium may further optionally contain LIF, penicillin/streptomycin, puromycin, L-glutamine, nonessential amino acids, β-mercaptoethanol, and the like.). After about 25 to about 30 days or more, ES-like colonies can be formed.

Moreover, cells may also be cultured under hypoxic conditions in which the oxygen concentration is 5%-10% to increase the efficiency of iPS cell induction (WO 2010/013845).

During the above culture, medium exchange with fresh medium is performed once a day from day 2 after the initiation of culture. In addition, the number of somatic cells to be used for nuclear reprogramming is not limited, but ranges from approximately $5 \times 10^3$ to approximately $5 \times 10^6$ cells per culture dish (100 cm$^2$).

When a gene such as a drug resistance gene is used as a marker gene, cells expressing the marker gene can be selected by culturing cells in a medium (a selection medium) containing the relevant drug. When a marker gene is a fluorescent protein gene, cells expressing the marker gene can be detected via observation under fluorescence microscopy. When a marker gene is a luminescent enzyme gene, cells expressing the marker gene can be detected through addition of a luminescent substrate. When a marker gene is a enzyme gene, cells expressing the marker gene can be detected through addition of a chromogenic substrate.

The term "somatic cell" as used herein refers to all animal cells excluding germ-line cells such as ova, oocytes and spermatocytes, totipotent cells, and ES cells (preferably, cells of mammals including humans). Examples of somatic cells include, but are not limited to, somatic cells of fetuses, somatic cells of neonates, and mature healthy or pathogenic somatic cells. Examples thereof also include primary cultured cells, passage cells, and cells of established cell lines. Examples thereof further include tissue stem cells and tissue precursor cells. Specific examples of somatic cells include, but are not limited to, (1) tissue stem cells (somatic stem cells) such as neural stem cells, hematopoietic stem cells, mesenchymal stem cells, and dental pulp stem cells, (2) tissue precursor cells, and (3) differentiated cells such as lymphocytes, epithelial cells, endothelial cells, muscle cells, fibroblasts (e.g., skin cells), hair cells, hepatocytes, gastric mucosal cells, enterocytes, splenocytes, pancreatic cells (e.g., pancreatic exocrine cells), brain cells, pneumocytes, renal cells, and skin cells.

(E) Embryo Clone-Derived ES Cells Obtained by Nuclear Transplantation

Nuclear transfer (nt) ES cells are embryo clone-derived ES cells prepared by nuclear transplantation techniques, having properties almost the same as those of fertilized egg-derived ES cells (T. Wakayama et al. (2001), Science, 292: 740-743; S. Wakayama et al. (2005), Biol. Reprod., 72: 932-936; J. Byrne et al. (2007), Nature, 450: 497-502). Specifically, ES cells established from the inner cell masses of an embryo clone-derived blastocysts obtained by substitution of the nucleus of an unfertilized egg with the nucleus of a somatic cell are nt ES (nuclear transfer ES) cells. For preparation of nt ES cells, the nuclear transplantation technique (J. B. Cibelli et al. (1998), Nature Biotechnol., 16: 642-646) and the ES cell preparation technique (see above) are used in combination (Kiyoka Wakayama et al., (2008), Experimental Medicine, Vol. 26, No. 5 (Suppl.), pp. 47-52). Through nuclear transplantation, the nucleus of a somatic cell is injected into an enucleated mammalian unfertilized egg followed by several hours of culture, so that reprogramming can be performed.

<Small Molecule BMP Inhibitor>

A small molecule BMP inhibitor that can be used in the present invention is a small molecule inhibitor involved in inhibition of the BMP signaling that is mediated by binding of BMP (bone morphogenetic protein) to a BMP receptor (type I or type II), but differs from a protein inhibitor such as Noggin, chordin, follistatin, or the like that is a natural inhibitor. As used herein, the term "small molecule" means an organic or inorganic molecule and this term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). This inhibitor should have effects of inducing the differentiation of pluripotent stem cells into neural precursor cells. Examples of a small molecule BMP inhibitor having such properties include a compound that inhibits BMP2, BMP4, BMP6 or BMP7 capable of activating a transcription factor SMAD1, SMAD5, or SMAD8, such as Dorsomorphin (that is, 6-[4-(2-piperidin-1-yl-ethoxy)phenyl]-3-pyridin-4-yl-pyrazolo [1,5-a]pyrimidine) and a derivative thereof (P. B. Yu et al. (2007), Circulation, 116: II_60; P. B. Yu et al. (2008), Nat. Chem. Biol., 4: 33-41; J. Hao et al. (2008), PLoS ONE (www.plozone.org), 3 (8): e2904). Dorsomorphin is commercially available from Sigma-Aldrich, for example. Dorsomorphin has biological activity to inhibit the above BMP signaling by inhibiting the binding of BMP to a BMP receptor. In addition to them, examples of a BMP I-type receptor kinase inhibitor include LDN-193189 (that is, 4-(6-(4-(piperazin-1-yl)phenyl)pyrazolo[1,5-a]pyrimidin-3-yl) quinoline) and a derivative thereof (Yu P B et al. Nat Med, 14: 1363-9, 2008). LDN-193189 is commercially available from Stemgent, for example.

<Small Molecule TGFβ Family Inhibitor>

According to the present invention, the induction efficiency of the differentiation of pluripotent stem cells into neural precursor cells can be significantly improved by combining the above small molecule BMP inhibitor with a small molecule TGFβ (transforming growth factor β) family inhibitor.

The term "small molecule TGFβ family inhibitor" as used herein refers to a small molecule inhibitor that interferes with the signaling of the TGFβ family. Examples of such small molecule TGFβ family inhibitor include SB431542, SB202190 (R. K. Lindemann et al., Mol. Cancer 2: 20 (2003)), SB505124 (GlaxoSmithKline), NPC30345, SD093, SD908, SD208 (Scios), LY2109761, LY364947, LY580276 (Lilly Research Laboratories), and A-83-01 (WO 2009146408). SB431542 (4-[4-(1,3-benzodioxol-5-yl)-5-(2-pyridinyl)-1H-imidazol-2-yl]benzamide) or A-83-01 (3-(6-methylpyridin-2-yl)-1-phenylthiocarbamoyl-4-quinolin-4-ylpyrazole) is preferred.

TGFβ family members regulate cellular process and development process such as mitosis, cell differentiation, embryonic pattern formation, and organogenesis. For example, the TGFβ signaling is carried out via a heteromeric receptor complex of serine-threonine kinase receptor type I and type II. This complex activates the process of downstream Smad signaling. Specifically, when TGFβ binds to the receptor complex, the TGFβ-type II receptor phosphorylates the TGFβ-type I receptor and then the TGFβ-type I receptor phosphorylates receptor-mediated Smad (R-Smad), so that downstream response is initiated. Activated R-Smad and Smad4 form a multimeric complex, so that the activated R-Smad is transferred to the nucleus and then the transcriptional regulation of a target gene is induced.

When such TGFβ family signaling is inhibited, differentiation of pluripotent stem cells into neural precursor cells is induced. Furthermore, when the above BMP signaling is inhibited in addition to this inhibition, not only the rate of inducing neural precursor cells is increased, but also the residual rate of undifferentiated cells (i.e., pluripotent stem cells) is more decreased, thus, the rate of conversion into neural precursor cells is increased.

Snyder et al. (US 2011/0002897) discloses inducing neural stem cells by exposing pluripotent stem cells to factors that activate both the PI3K and MAPK signaling pathways and factors that inhibit the TGF-β superfamily and the Wnt signaling pathways. However, in the method of the present application, factors inhibiting the Wnt signaling pathways are not required.

<Feeder Cells>

In the present invention, feeder cells are not always required, but feeder cells may be present. Examples of feeder cells include embryonic fibroblasts and stromal cells. Examples of embryonic fibroblasts include MEF (mouse embryonic fibroblasts), STO cells (mouse embryonic fibroblast cell line), and SNL cells (subclones of STO cells; e.g., SNL 76/7 cells). Also, examples of stromal cells include PA6 cells (mouse stromal cell line (RIKEN BRC Cell Bank (Japan)), MS-5 cells (Exp Hematol. 17: 145-53 (1989)), and OP9 cells (Science. 265: 1098-1101 (1994)). The SDIA method comprises coculturing ES cells with stromal cells and particularly with PA6 cells, so as to perform almost selective differentiation into neural precursor cells. According to the present invention, even in the absence of feeder cells, selective differentiation into neural precursor cells can be induced only by making the above small molecule BMP inhibitor or a combination of the small molecule BMP inhibitor and the above small molecule TGFβ family inhibitor, present in a differentiation induction medium. The use of feeder cells in addition to such culture conditions can further improve the efficiency of differentiation into neural precursor cells.

However, if so, when transplantation of neural precursor cells, or neural or glial cells that differentiate therefrom, into a mammal such as a human is taken into consideration, it goes without saying that the use of cells that are heterogenous to donors should be avoided to as great an extent as possible.

<Induction of Differentiation of Neural Precursor Cells>

(A) Differentiation Medium

Medium used for culturing animal cells can be prepared as basal medium. Examples of such basal medium include IMDM medium, medium 199, Eagle's Minimum Essential Medium (EMEM), aMEM medium, Doulbecco's modified Eagle's Medium (DMEM), Ham's F12 medium, RPMI 1640 medium, Fischer's medium, Glasgow MEM, and mixtures thereof. Medium may contain serum or may be serum free.

Medium may further contain, if necessary, one or more serum substitutes, such as albumin, transferrin, Knockout Serum Replacement (KSR) (serum substitute for FBS upon ES cell culture), fatty acid, insulin, a collagen precursor, trace elements, 2-mercaptoethanol, 3'-thiol glycerol, B27-supplement, and N2-supplement, as well as one or more substances such as lipids, amino acids, nonessential amino acids, vitamins, growth factors, cytokines, antibiotics, antioxidants, pyruvate, a buffering agent, and inorganic salts.

Medium may also contain the above small molecule BMP inhibitor and/or optionally the above small molecule TGFβ family inhibitor. Medium may further contain a culture supernatant of the above feeder cells. Medium may further contain any of ERK (extracellular signal-regulated kinase) inhibitors.

An example of the differentiation medium is DMEM/Ham's F12 mixed medium containing 5% knockout serum replacement (KSR), 2 mM L-glutamine, nonessential amino acids, and 1 µM 2-mercaptoethanol (2-ME) or Glasgow MEM containing 8% KSR, 1 µM 2ME pyruvate and Nonessential amino acids, as described in Examples shown below.

(B) Method for Inducing Differentiation

According to the present invention, upon induction of differentiation of pluripotent cells such as ES cells or iPS cells into neural precursor cells, such cells are prepared and then cultured using the methods described in the above documents. When human ES cells or human iPS cells are cultured, a medium for primate ES cells (ReproCELL (Kyoto, Japan)) can be preferably used.

Induction of differentiation of pluripotent stem cells into neural precursor cells can be performed in either the presence or absence of feeder cells using the above-described differentiation media. When feeder cells are present, as such cells, the above-exemplified MEF (mouse embryonic fibroblasts), STO cells (mouse embryonic fibroblast cell line), PA6 cells (mouse stromal cell line (RIKEN BRC Cell Bank (Japan)), SNL cells (subclones of STO cells; e.g., SNL 76/7 cells), and the like can be used. For feeder cells, mitomycin C treatment is generally performed to stop cell proliferation.

Immediately before and immediately after differentiation induction, preferably, a ROCK (p160-Rho-associated coiled-coil kinase) inhibitor is added to a medium containing cultured pluripotent stem cells. The ROCK inhibitor is a substance exhibiting very strong effects of suppressing cell death upon cell dispersion. For example, Y-27632, Fasudil (HA-1077), or the like is known as such a ROCK inhibitor (K. Watanabe et al., Nat. Biotech., 25: 681-686 (2007)). The concentration of an inhibitor ranges from, but is not limited to, about 50 nM to about 10 µM per culture dish.

Density of pluripotent stem cells in a medium preferably ranges from approximately $5.0 \times 10^4$ to approximately $1.0 \times 10^7$ cells, but it may fall outside of such range.

Examples of culture include three-dimensional culture under non-adhesion conditions, such as suspension culture (e.g., dispersion culture and aggregation-suspension culture), two-dimensional culture under adhesion conditions, such as plate culture, and continuously combined cultures which constitute a three-dimensional culture and then a two-dimensional culture. When the differentiation is induced in the presence of feeder cells, two-dimensional culture can be employed. On the other hand, in the absence of feeder cells, three-dimensional culture can be employed.

In the case of a cell adhesive incubator, for the purpose of improving adhesion properties with cells, the surface of the incubator may be coated with a cell-supporting substance, such as collagen, gelatin, poly-L-lysine, poly-D-lysine, laminin, fibronectin, or Matrigel™ (Becton, Dickinson and Company).

In dispersion culture, pluripotent stem cells are cultured in a state suspended in a liquid medium. Also, pluripotent stem cell masses (or embryoid bodies) are formed by aggregation-suspension culture. Subsequently, differentiation of the cell masses (or embryoid bodies) into cells of interest can be induced. For the aggregation-suspension culture, the embryoid body culture method (Keller et al., Curr. Opin. Cell Biol. 7, 862-869 (1995)) or the SFEB method (e.g., Watanabe et al., Nature Neuroscience 8, 288-296 (2005); WO 2005/123902) can be used, for example. Preferable method is culture of embryoid bodies in a medium without serum like SFEB method.

In adhesion culture, the Matrigel method (Chambers S M, et al. Nat Biotechnol. 27: 485, 2009) or the SDIA method (Kawasaki H, et al. Neuron. 28:31-40, 2000 or Kawasaki H, et al. Proc Natl Acad Sci U.S.A. 99: 1580-5, 2002) can be used, for example.

Regarding culture conditions, the above mentioned media can be used and the temperature for culture is not limited to the following examples, but ranges from about 30° C. to 40° C., preferably about 37° C. Culture is performed under an atmosphere of $CO_2$-containing air, wherein the $CO_2$ concentration preferably ranges from about 2% to 5%. The time for culture or the schedule for culture ranges from 7 days to 21 days, more preferably 14 days under differentiation induction conditions, for example.

Regarding specific methods and conditions for differentiation induction, see Examples given below.

<Induced Neural Precursor Cells>

The present invention also provides induced neural precursor cells prepared by the method for inducing differentiation as described above.

Examples of neural precursor cells that can be obtained by the method of the present invention include precursor cells of all neural cells, such as neural cells in the central nervous system, neural cells in the peripheral nervous system, motor neurons, neural cells in the sensory organ system, and neural cells in autonomic nerve.

Neural precursor cells can be identified using expression markers such as expression markers for primitive neuroectoderm or neural stem cells (e.g., a neural cell adhesion molecule (NCAM), polysialylated NCAM, A2B5 (expressed in neural cells of fetuses or neonates), intermediate filament proteins (nestin, vimentin, or the like), and a transcription factor Pax-6), dopamine neuron markers (e.g., tyrosine hydroxylase (TH)), and neural markers (e.g., TuJ1), for example.

After preparation, neural precursor cells may be directly transplanted into a living body or may be completely or partially differentiated into neural cells or glial cells (including astrocytes and oligodendrocytes) and then transplanted into a living body.

<Use in Screening for a Therapeutic Agent for Neurological Disease>

The induced neural precursor cells of the present invention can also be used for screening for compounds for treating neurological diseases (e.g., pharmaceutical compounds, solvents, small molecules, peptides, or polynucleotides). For example, a candidate pharmaceutical compound alone or the same combined with another drug is added to induced neural precursor cells or neural cells more mature than the precursor cells, and then evaluation can be performed based on morphological or functional changes of the cells. Evaluation can be performed by measuring an amount of dopamine produced from the cells as an example of a functional change. Here, induced neural precursor cells are: preferably cells presenting a phenotype similar to that of a neurological disease to be treated; and particularly preferably induced pluripotent stem cells prepared from somatic cells affected by neurological diseases, or induced neural precursor cells prepared by inducing the differentiation of ntES cells in which the nuclei of disease-affected somatic cells have been transplanted.

<Applying to Regenerative Medicine>

The induced neural precursor cells of the present invention can be effectively used in the field of regenerative medicine for normalization of a damaged nervous system tissue. Therefore, the induced neural precursor cells can be used as cells for treating diseases associated with damages of any cells in the nervous system.

Examples of such diseases include ischemic brain disease (e.g., stroke), brain traumas, spinal injuries, motor neurologic diseases, neurodegenerative diseases, retinitis pigmentosa, age-related macular degeneration, inner ear hearing loss, multiple sclerosis, amyotrophic lateral sclerosis, spinocerebellar degeneration, Huntington's disease, Alzheimer's disease, Parkinson's disease, epilepsy, and schizophrenia.

Also, when cells are used for therapy, the purity of the cells should desirably be increased. Examples of such purification include a method for selection of cells of interest, e.g. flow cytometry, and a treatment of cells in a medium containing an anticancer agent. Flow cytometry is performed by applying cell particles into a very thin liquid flow at a high rate, irradiating with a laser beam, and then measuring light such as fluorescence (when the cells are fluorescent-labeled in advance) or scattered light emitted from particles. When a cell sorter is provided, cells of interest can be selected and separated. Cells can be fluorescent-labeled using an antibody (fluorescent-labeled) specific to the neural precursor cells, such as an anti-Nestin antibody. Also, through treatment in a medium containing an anticancer agent, undifferentiated cells can be removed. Examples of such anticancer agent include mitomycin C, 5-fluorouracil, adriamycin, and methotrexate.

Neural precursor cells can be transplanted into sites of diseases by a technique described in Nature Neuroscience, 2, 1137 (1999) or N Engl J Med.; 344: 710-9 (2001), for example.

EXAMPLES

The present invention will hereafter be described in more detail with reference to the following examples, although the technical scope of the present invention is not limited thereto.

Methods

Cells and Culture

Human ES cells (KhES-1, KhES-2, and KhES-3) from the Institute for Frontier Medical Sciences, Kyoto University were provided, and they were then cultured by the known method (Suemori H, et al. Biochem Biophys Res Commun. 345: 926-32, 2006). Human iPS cells (G1, G4, B6, and B7) were provided by Dr. Yamanaka of Kyoto University and then cultured by the known method (Takahashi K, et al. Cell. 131: 861-72, 2007 and Nakagawa M, et al. Nat Biotechnol. 26: 101-6, 2008). PA6 cells (RIKEN BRC Cell Bank) were seeded on a gelatin-coated dish and then cultured using MEM alpha containing 10% FBS. Upon induction of differentiation, cells were cultured for at least one day, confirmed to be confluent, and then used as feeder cells. Human iPS cells (404C2) was established by introducing reprogramming factors (OCT3/4, SOX2, KLF4, L-MYC, LIN28, and shRNA for p53) into human fibroblast using a vector containg EBNA-1 and oriP (U.S. 61/232,402 and U.S. 61/307,306), then cultured by same method of other human iPS cells.

Induction of Differentiation into Neural Precursor Cells (in the Presence of Feeder Cells: SDIA Method)

ES cells or iPS cells were cultured using STO cells as feeder cells. One day before the initiation of differentiation induction, 10 μM ROCK inhibitor (Y27632) was added into a medium. CTK dissociation solution (0.25% Trypsin, 1 mg/ml Collagenase and KSR 20%, and 1 mM $CaCl_2$) was added at 500 μl/10 cm dish, followed by 3 to 5 minutes of incubation at 37° C. The dish was gently tapped to remove feeder cells. After washing once with PBS, the CTK dissociation solution was added again, followed by 10-15 minutes of incubation at 37° C. ES cells or iPS cells detached from the dish were suspended in 5 ml of differentiation medium (DMEM/Ham's F12 containing 5% knockout serum replacement (KSR), 2 mM L-glutamine, non-essential amino acids, and 1 μM 2-mercaptoethanol (2-ME)). After centrifugation, supernatants were removed. Again, the cells were suspended in 1 ml of the differentiation medium and then separated from each other by pipetting, so as to result in small aggregates (10-20 cells/clump).

The obtained small aggregates were seeded on dishes having PA6 as feeder cells at concentrations ranging from 2500 to 5000 cells/cm$^2$. As a medium, a differentiation medium containing 2 μM Dorsomorphin (Sigma) and/or 10 μM SB431542 (Sigma) and/or 300 ng/ml Noggin (HZ-1026: HumanZyme) or 2 μl/well DMSO was used. 10 μM Y27632 was added only in the initial culture. Medium exchange was not performed until day 7, and it was then performed once every 3 to 4 days.

Induction of Differentiation into Neural Precursor Cells (in the Absence of Feeder Cells: SFEBq Method)

By the above method, ES cells or iPS cells from which feeder cells had been removed were incubated for 5 minutes at 37° C. using 1 ml of Accumax™ for separation. After washing, the number of cells was counted. Cells were suspended in the above differentiation medium and then seeded onto a low adhesion 96-well plate (Lipidure-coat plate: NOF Corporation) at 9000 cells/well. For culture, a differentiation medium containing 2 μM Dorsomorphin and 10 μM SB431542 was used and 50 nM Y27632 was added only in the initial culture. Medium exchange was not performed until day 7, and then it was performed once every 3 days.

Induction of differentiation into neural cells using each drug (Matrigel method)

The iPS cells (G4) were separated by 20 minutes of Accutuase treatment, washed with a human ES cell medium, and then left on a gelatin coating dish for 1 hour with a ROCK inhibitor (Y27632)-containing medium, so that feeder cells were removed. Subsequently, ES cells or iPS cells (18000 cells/cm$^2$) were seeded on a Matrigel (BD) coating dish and then cultured for 3 days using an MEF conditioned medium supplemented with bFGF and a ROCK inhibitor (Y27632), so that the cells reached confluence (Y27632 was removed in mid-course).

Next, cells were cultured for 5 days in a differentiation medium (DMEM/F12, 20% knockout serum replacement (Gibco) and 0.1 mM 2-mercaptoethanol) containing 10 μM SB431542, 2 μM Dorsomorphin, 300 ng/ml Noggin, 1 nM-100 nM LDN-193189 (STEMGENT04-0019) or DMSO (control) or a combination thereof. Without addition of SB431542 on day 5, cells were continuously cultured in a differentiation medium supplemented with Dorsomorphin, Noggin, LDN-193189, or DMSO. At this time, the proportion of N2 medium (the medium prepared by adding an N2 supplement to DMEM/F12) was increased at two-day intervals up to 25%, 50%, and then 75% without changing the concentrations of other drugs.

Induction of Differentiation into Neural Cells Via Addition of LDN-193189 and SB431542 (SDIA Method)

On one day before the initiation of differentiation induction, CTK dissociation solution (0.25% Trypsin, 1 mg/ml Collagenase and KSR 20%, and 1 mM $CaCl_2$) was added to ES cells (KhES-1, KhES-4, and KhES-5), colonies were dissociated. ES cells detached from the dish were subjected to removal of MEF on gelatin coating, suspended in a differentiation medium (DMEM/Ham's F12 containing 5% knockout serum replacement (KSR), 2 mM L-glutamine, non-essential amino acids, and 1 μM 2-mercaptoethanol (2-ME)) for 1 hour, and then separated by pipetting so as to result in small aggregates (10-20 cells/clump). The obtained small aggregates were seeded on PA6 at a concentration ranging from 2500 to 5000 cells/$cm^2$. On day 4 of culture, the medium was exchanged with a differentiation medium supplemented with 10 μM SB431542 and 5-1,000 nM LDN-193189. Three days later, the medium was exchanged with a differentiation medium without SB431542 and LDN-193189. Thereafter, medium exchanges with such a differentiation medium without SB431542 and LDN-193189 were performed at 2- to 3-day intervals.

Investigation for Combination of Differentiation Induction Agents Under the Conditions of SFEBq Method One day before the initiation of differentiation induction from Human iPS cells (404C2), 10 μM ROCK inhibitor (Y27632) was added into a medium. CTK dissociation solution (0.25% Trypsin, 1 mg/ml Collagenase and KSR 20%, and 1 mM $CaCl_2$) was added at 500 μl/10 cm dish, followed by 3 to 5 minutes of incubation at 37° C. The dish was gently tapped to remove feeder cells. After washing once with PBS, dissociation was performed with 5 minutes of incubation at 37° C. with 1 ml Accumax®. After washing, the number of cells was counted. Cells were suspended in the above differentiation medium and then seeded onto a low adhesion 96-well plate (Lipidure-coat plate: NOF Corporation) at 9000 cells/well. After the cells were cultured with medium consisting of the following 6 combinations for 4 days, then the medium was change to above differentiation medium (DMEM/Ham's F12 containing 5% knockout serum replacement (KSR), 2 mM L-glutamine, non-essential amino acids, and 1 μM 2-mercaptoethanol (2-ME)). The differentiated cells were evaluated with undifferentiated marker (Nanog) and neural differentiated maker (Pax6 and Sox1).

A: old DFK5%+2 μM Dorsomorphin+10 μM SB431542

B: old GMK8%+100 nM LDN913189+0.5 μM A-83-01

C: DFK5%+2 μM Dorsomorphin+10 μM SB431542

D: GMK8%+100 nM LDN913189+0.5 μM A-83-01

E: GMK8%+100 nM LDN913189+10 μM SB431542

F: GMK8%+100 nM LDN913189+0.5 μM A-83-01+0.5 μM PD0325901 wherein i) "old" means 20 days passage after preparation.

ii) GMK8% means the medium consisting of Glasgow MEM (Invitrogen), 8% KSR, 1 μM 2ME, pyruvate and Non-essential amino acids.

iii) A-83-01 was purchased from Sigma-Aldrich Inc., and PD0325901 was purchased from Wako, Japan.

Immunostaining

On day 14 after differentiation induction, cells were fixed with 4% PFA for 30 minutes at 4° C. and then immunostained in PBS with each antibody listed in Table 1.

TABLE 1

List of antibodies

| Antigen | Model number | Sales company | Dilution ratio |
|---|---|---|---|
| Nestin | MAB5326 | Chemicon | 1:500 |
| Oct3/4 | SC9081 | SantaCruz | 1:500 |
| Pax6 | PRB-278P-100 | Covance | 1:200 |
| Nanog | AF1997 | R&D Systems | 1:200 |
| PSA-NCAM | — | Chemicon | 1:100 |
| SSEA3 | — | Chemicon | 1:100 |

FACS

Cells were incubated using Accumax™ for 20 minutes at 37° C. for separation and then analyzed using FACS Aria2. For analysis, cells were stained with a PSA-NCAM antibody or SSEA-4-PE conjugated antibody or Oct3/4 antibody or SSEA-1 antibody or Tuj1 antibody and dead cells were removed using 7AAD staining as an indicator or Red dye Live/dead fixable dead cell stain kit (Invitrogen).

Real Time PCR

RNA was collected using RNeasy plus Mini (QIAGEN) from ES cells or iPS cells from which feeder cells had been removed by the above method and then analyzed by a Thermal Cycler Dice Real Time system TP800 (TaKaRa) using SYBR Premix Ex Taq (TaKaRa).

Statistics

With the use of GraphPad Prism 5 (GraphPad Software), analysis was conducted (n=4) by one-way ANNOVA, post hoc (Dunnett's Multiple Comparison test).

Figure 1:
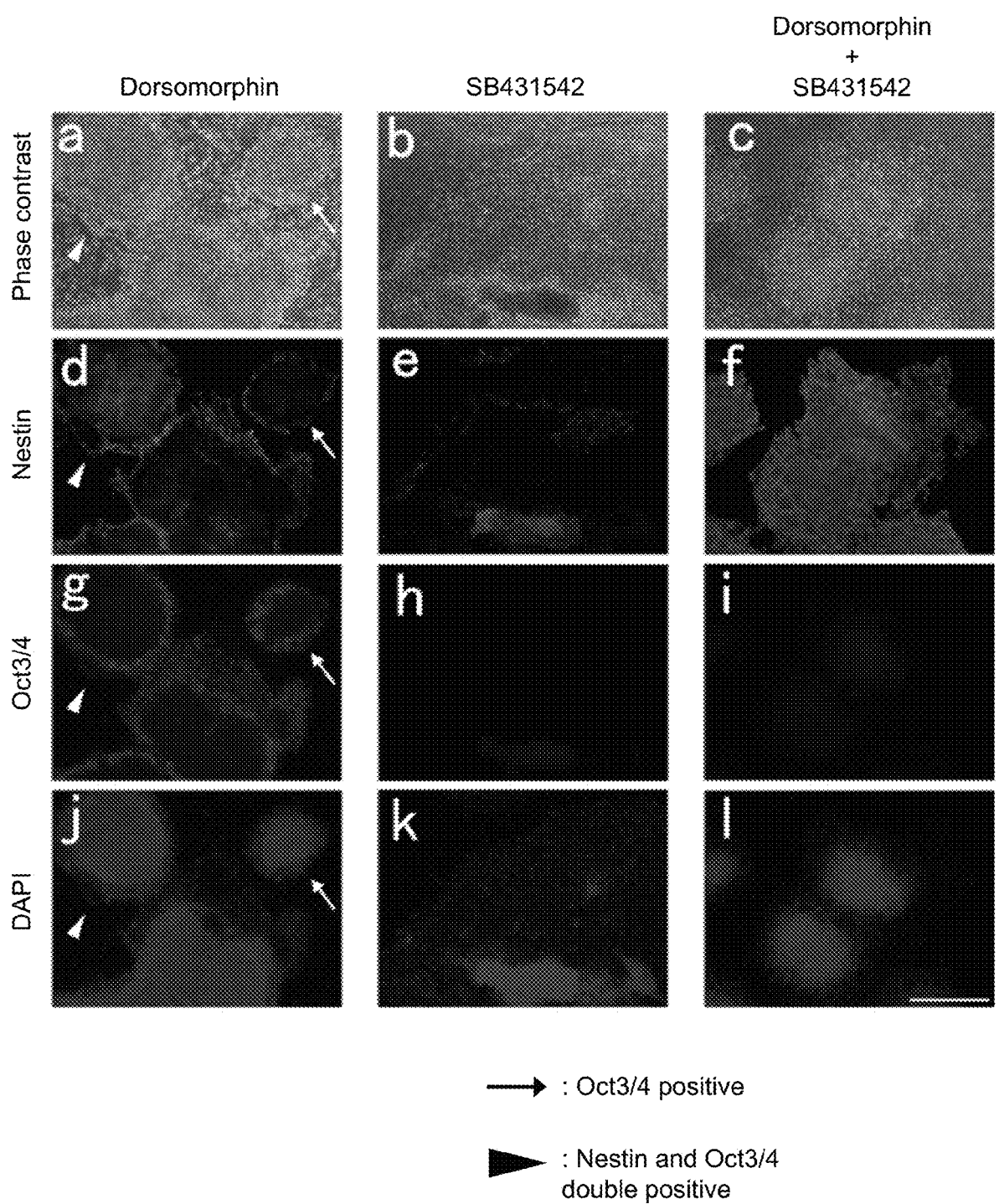
FIG. 1 shows phase contrast microscopic images (FIG. 1A-FIG. 1C), immunostaining images (FIG. 1D-FIG. 1F) obtained using anti-Nestin antibody, immunostaining images (FIG. 1G-FIG. 1I) obtained using anti-Oct3/4 antibody, and immunostaining images (FIG. 1J-FIG. 1L) obtained using DAPI, on day 14 after differentiation induction.
Figure 2:
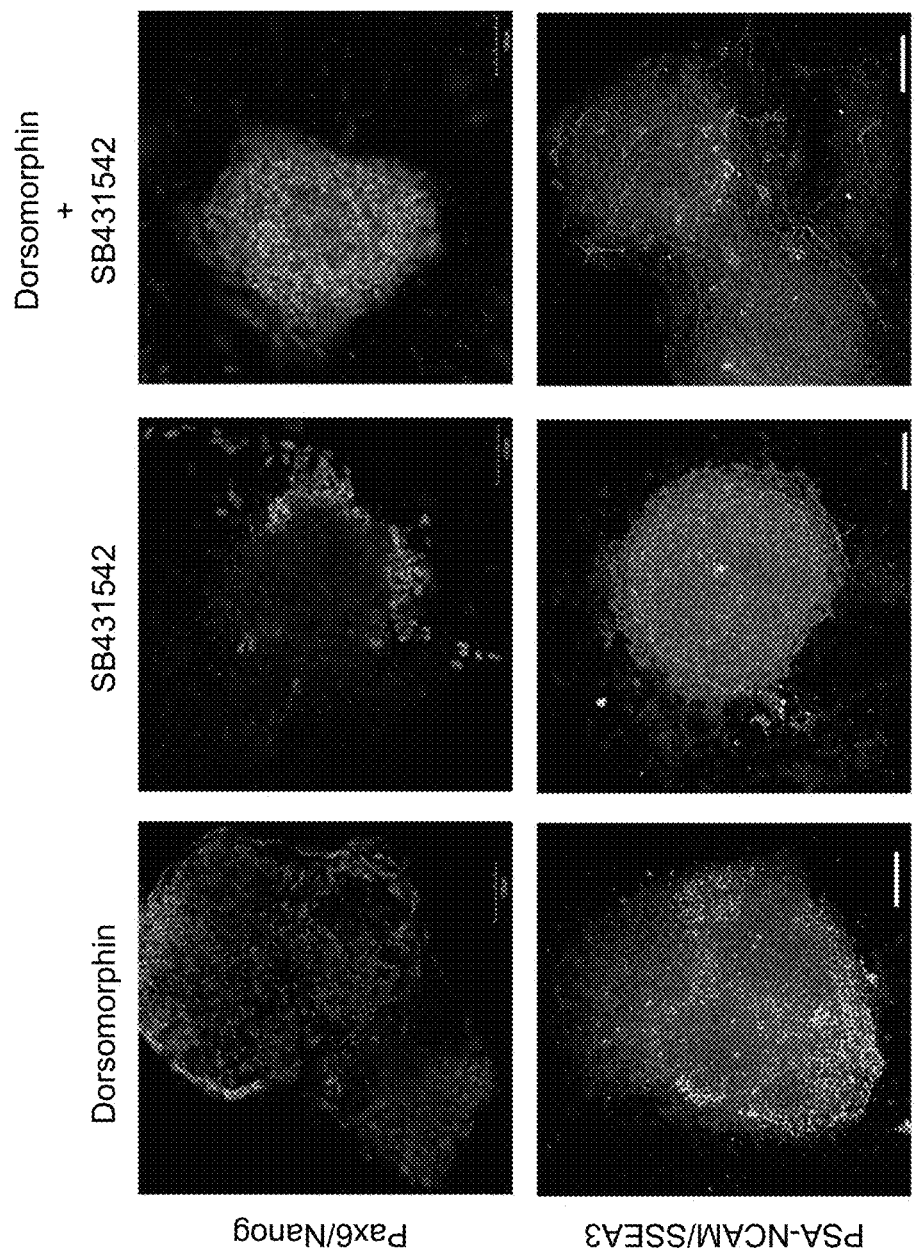
FIG. 2 shows immunostaining images obtained using anti-Pax6 antibody (green) and anti-Nanog antibody (red), and immunostaining images obtained using anti-PSA-NCAM antibody (green) and anti-SSEA3 antibody (red), on day 14 after differentiation induction.
Figure 3:
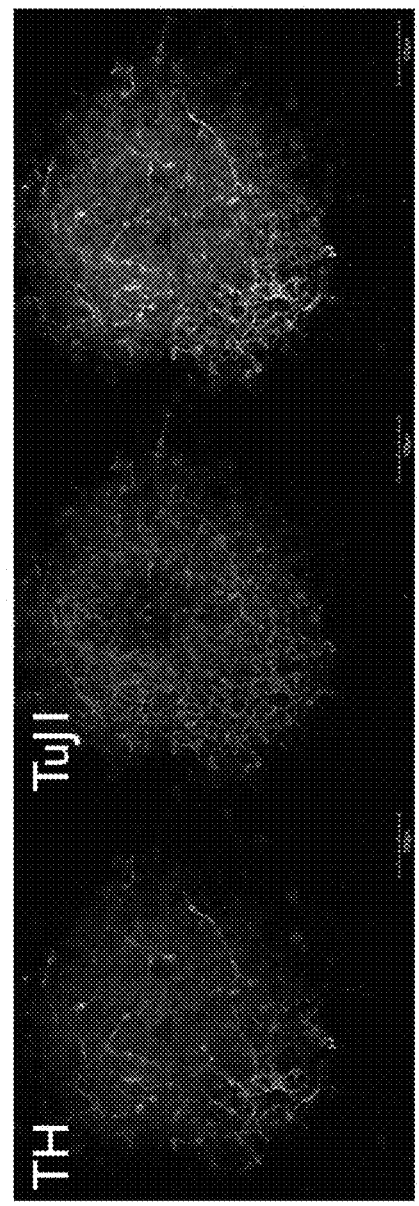
FIG. 3 shows an immunostaining image obtained using anti-TH (tyrosine hydroxylase) antibody (green) and anti-TuJ1 antibody (red) on day 21 after differentiation induction.

Example 1 iPS cells (G4) were cultured for 14 days using PA6 cells as feeder cells under three conditions: Dorsomorphin addition group (D group); SB431542 addition group (S group); and Dorsomorphin and SB431542 addition group (D+S group). Thus, differentiation induction was performed. As a result, in the D group, colonies positive for both Nestin and Oct3/4 were confirmed. In the S group, aggregated cell populations were confirmed in flatly spread cell groups. The aggregated cell populations were positive for Nestin. However, in the D+S group, almost all colonies were found to be positive for Nestin and almost no Oct3/4-positive colonies were observed (FIG. 1). Immunostaining was performed using the other undifferentiation marker, Nanog or SSEA3, and a neural marker, Pax6 or PSA-NCAM. As a result, it was similarly confirmed as follows: in the D group, undifferentiated cells and neural precursor cells coexisted; in the S group, neural precursor cells appeared in aggregated cell populations; and in the D&S group, cells were differentiated almost completely into neural precursor cells (FIG. 2). Next, the D+S group was subjected to 21 days of differentiation induction, so that cells positive for a dopamine neuron marker, TH (tyrosine hydroxylase) and a nervous marker, TuJ1, were confirmed (FIG. 3). As described above, it was confirmed that the differentiation of iPS cells into neural cells could be efficiently induced by culturing iPS cells using PA6 cells as feeder cells under conditions in which Dorsomorphin and SB431542 had been added.

Figure 4:
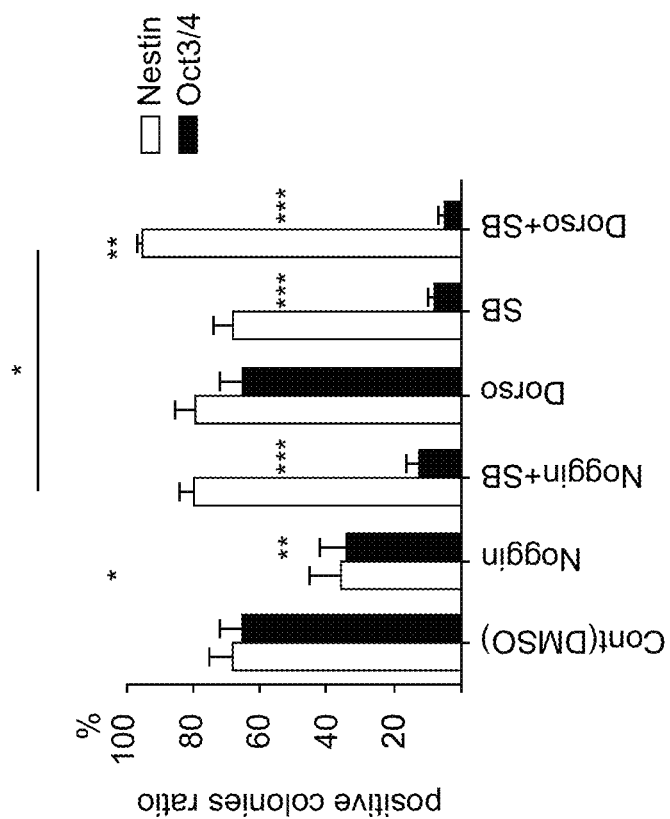
FIG. 4 shows.
Figure 4:
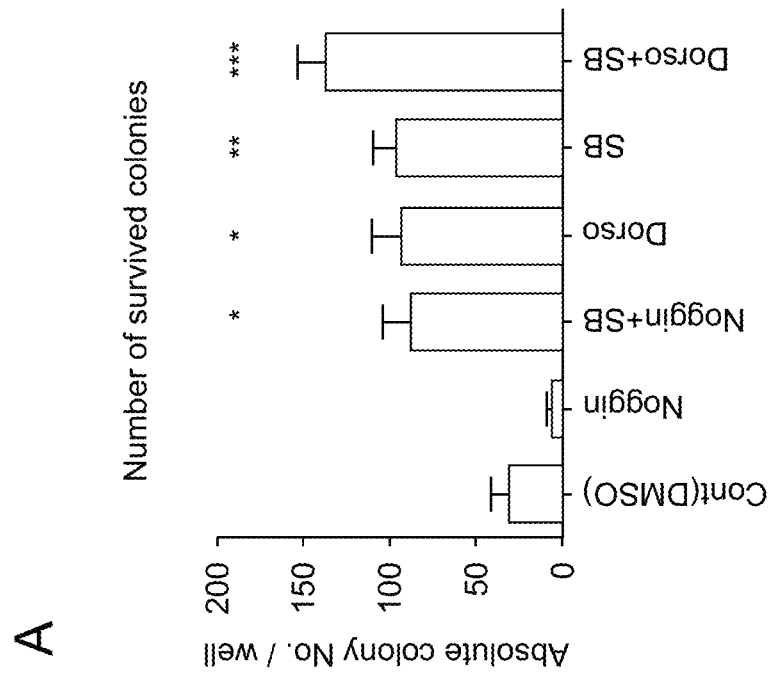

Next, ES cells (KhES-1, KhES-2, and KhES-3) and other iPS cells (G1, B6, and B7) were subjected to differentiation induction by a similar method. FIG. 4 shows the summary of results for 7 types (KhES-1, KhES-2, KhES-3, G1, G4, B6, and B7) of cell lines. It was confirmed that the number of colonies of a group to which either Dorsomorphin or SB431542 or both had been added or to which both thereof had been added was significantly higher than the number of colonies of a control group or a group to which Noggin (BMP-antagonistic protein) had been added (FIG. 4A). Therefore, it was confirmed that the above drugs had effects of contributing to the survival of pluripotent cells (ES cells and iPS cells) upon differentiation induction. Meanwhile, it was confirmed in induction of the differentiation into colonies containing neural cells that SB431542 was effective in elimination of undifferentiated cells (FIG. 4B). Also, the production efficiency of colonies containing neural cells was significantly higher with the combination of Dorsomorphin and SB431542 than with the combination of Noggin and SB431542.

Figure 5:
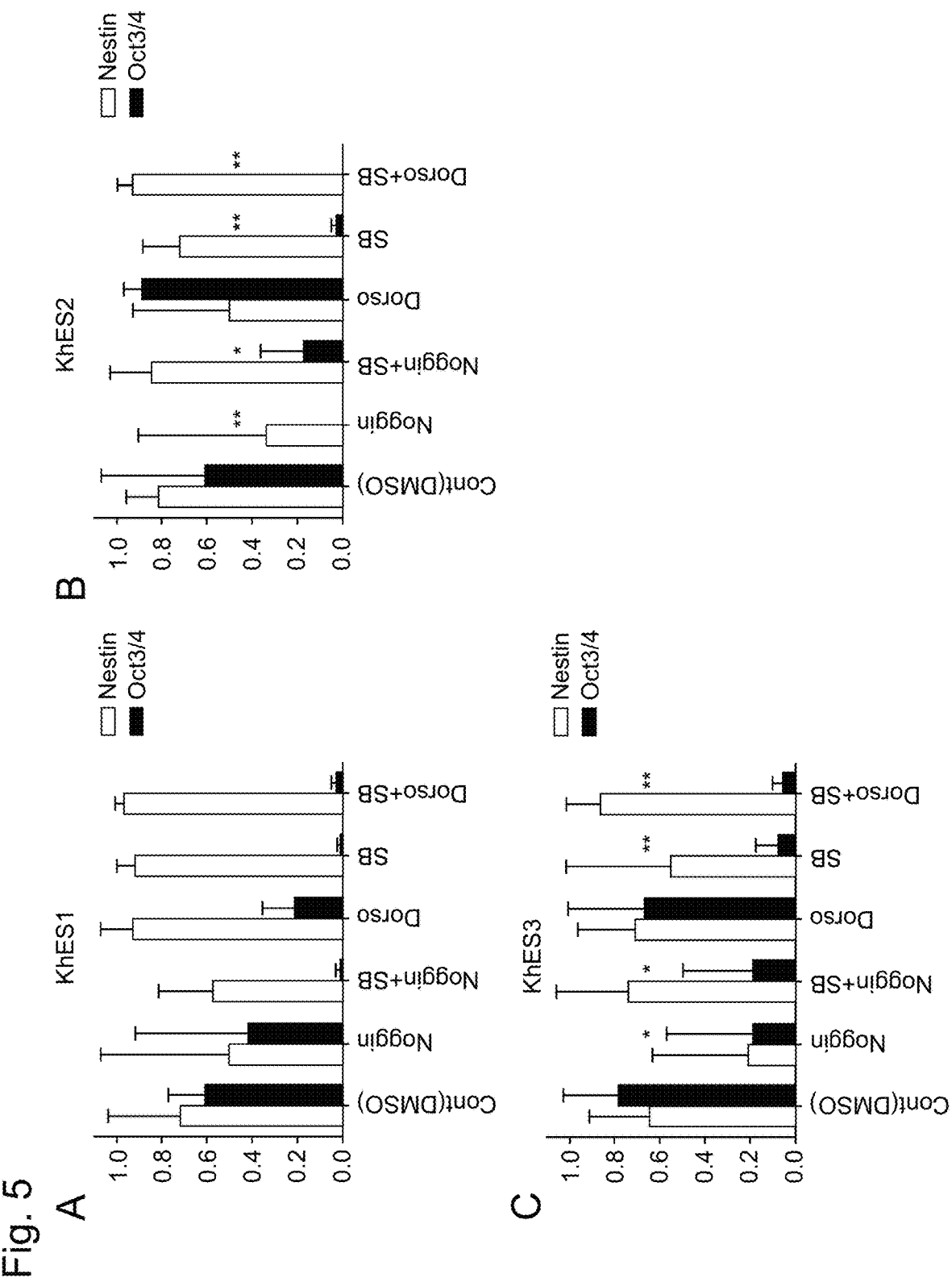
FIG. 5 shows the ratios of neural cell-containing colonies (positive for Nestin) to undifferentiated cell-containing colonies (positive for Oct3/4) existing per well on day 14 after differentiation induction of each ES cell line (KhES-1 (FIG. 5A), KhES-2 (FIG. 5B), or KhES-3 (FIG. 5C)).
Figure 6:
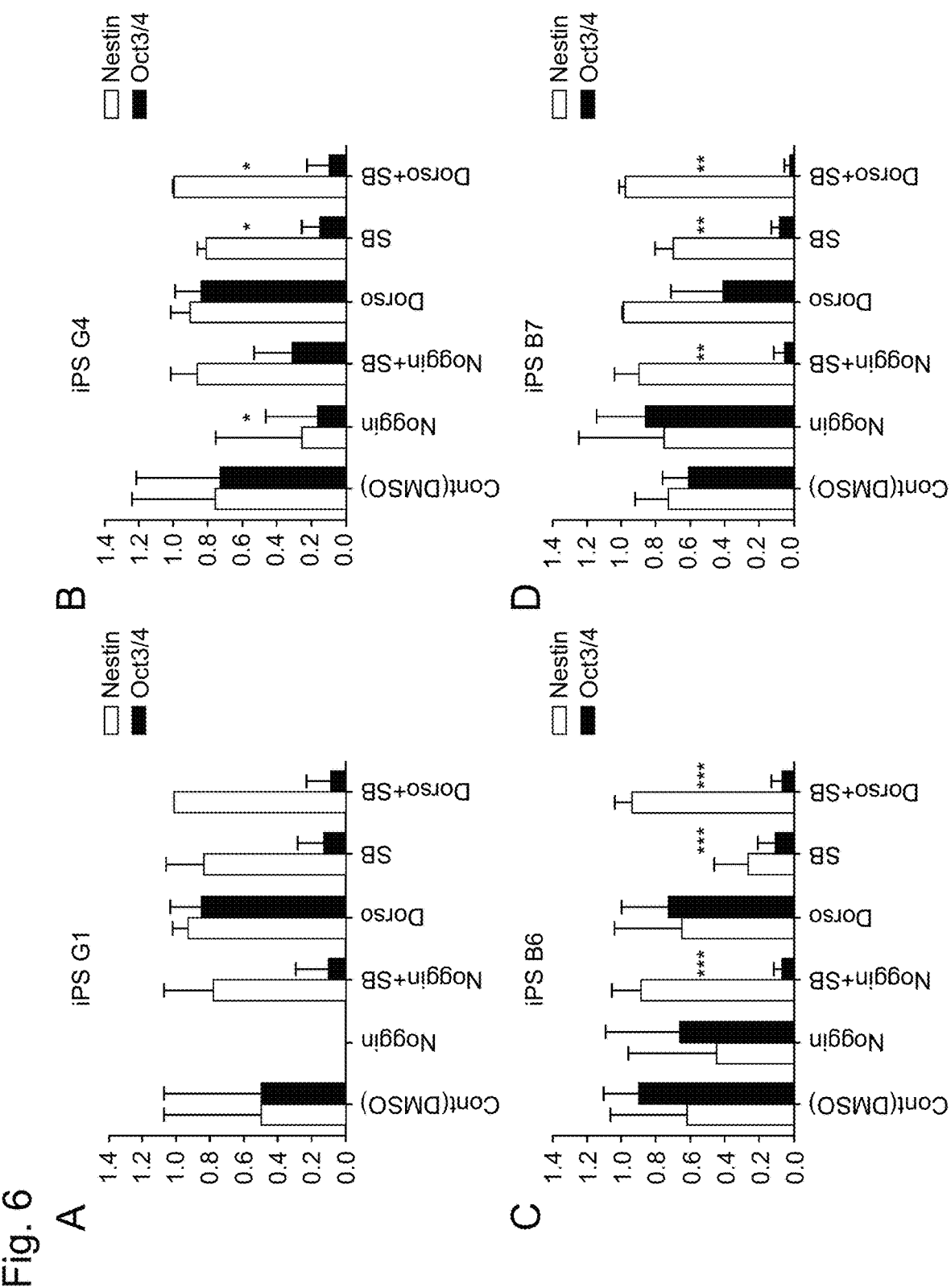
FIG. 6 shows the ratios of neural cell-containing colonies (positive for Nestin) to undifferentiated cell-containing colonies (positive for Oct3/4) existing per well on day 14 after differentiation induction of each iPS cell line (G1 (FIG. 6A), G4 (FIG. 6B), B6 (FIG. 6C), or B7 (FIG. 6D)).
Figure 7:
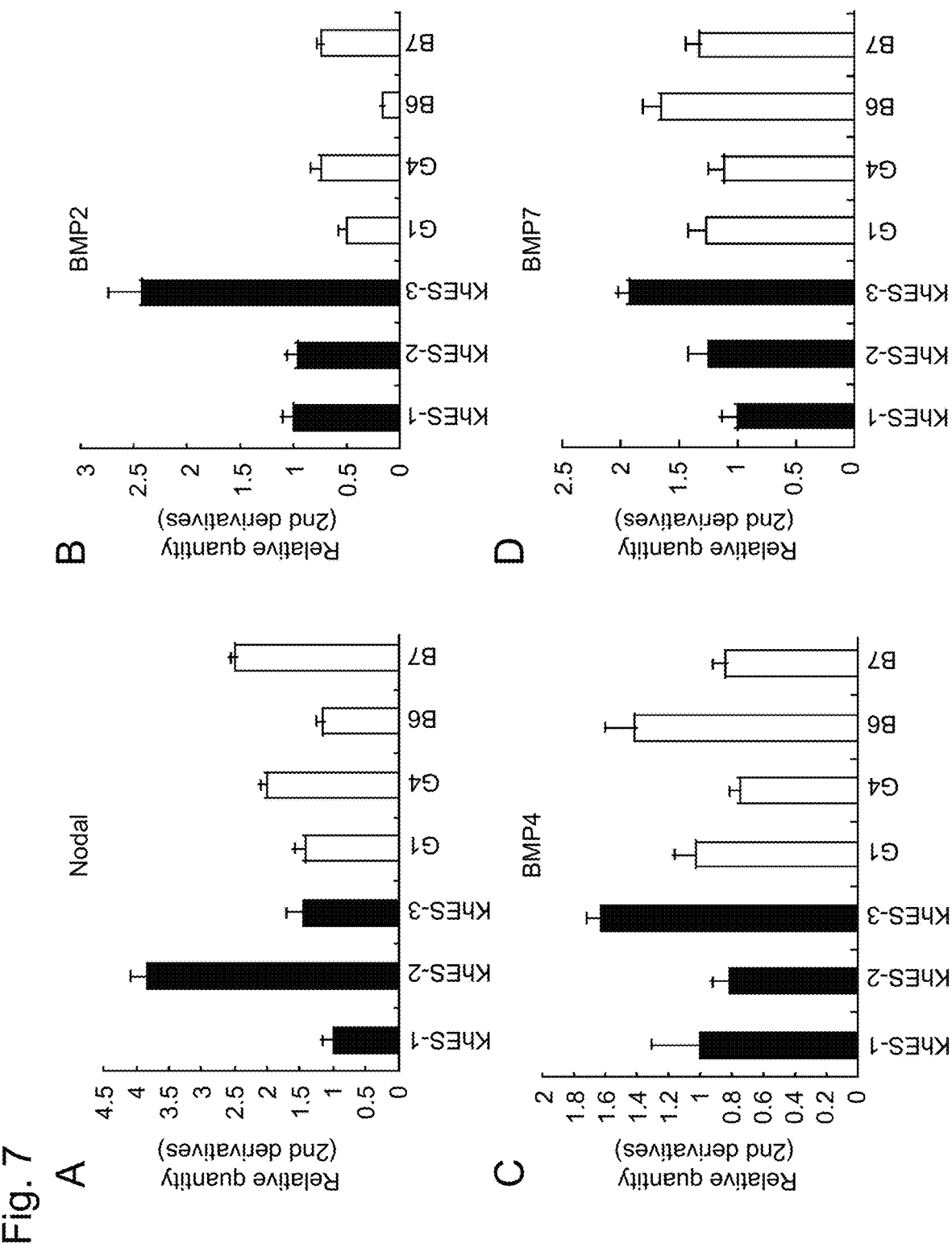
FIG. 7 shows mRNA expression levels in undifferentiated ES cells (KhES-1, KhES-2, and KhES-3) or iPS cells (G1, G4, B6, and B7) as measured by real time PCR with respect to Nodal (FIG. 7A), BMP2 (FIG. 7B), BMP4 (FIG. 7C), and BMP7 (FIG. 7D).

Similar tendencies were observed for individual cell lines (ES cells (FIG. 5) and iPS cells (FIG. 6)). These results can also be understood from the result that the expression of target proteins for the above drugs (TGF/Actibin/Nodal: SB431542; BMP: Dorsomorphin) remained almost the same for each cell line (FIG. 7).

Figure 8:
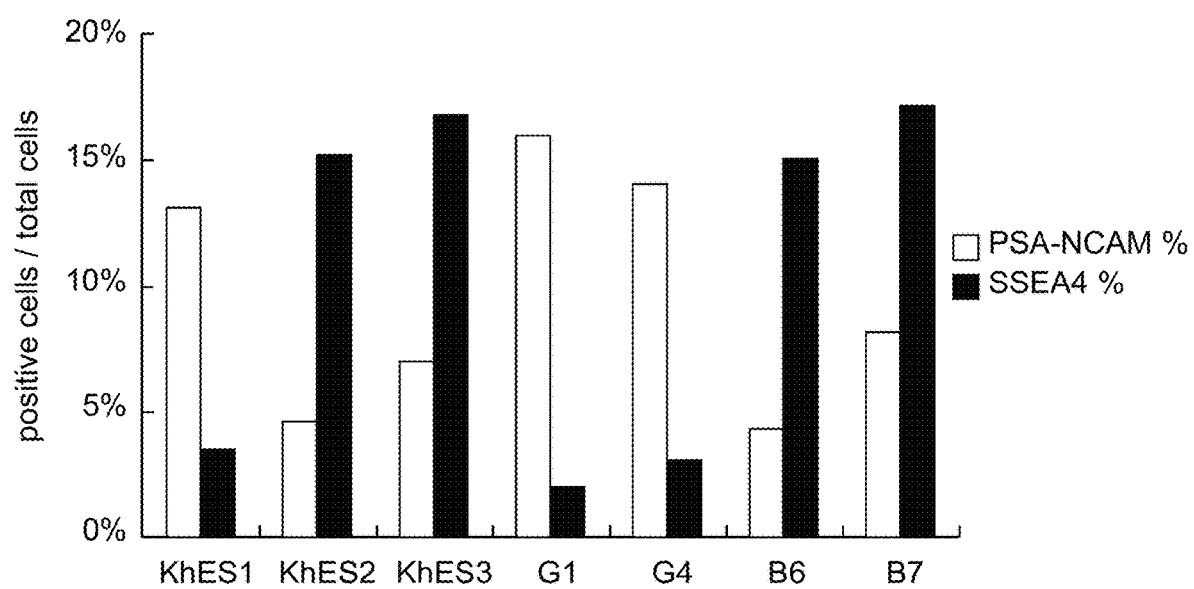
FIG. 8 is a graph showing PSA-NCAM positive (green) and SSEA4 positive (red) cell contents of each cell line on day 14 after differentiation induction only on PA6 cells without using Dorsomorphin and SB431542.
Figure 9:
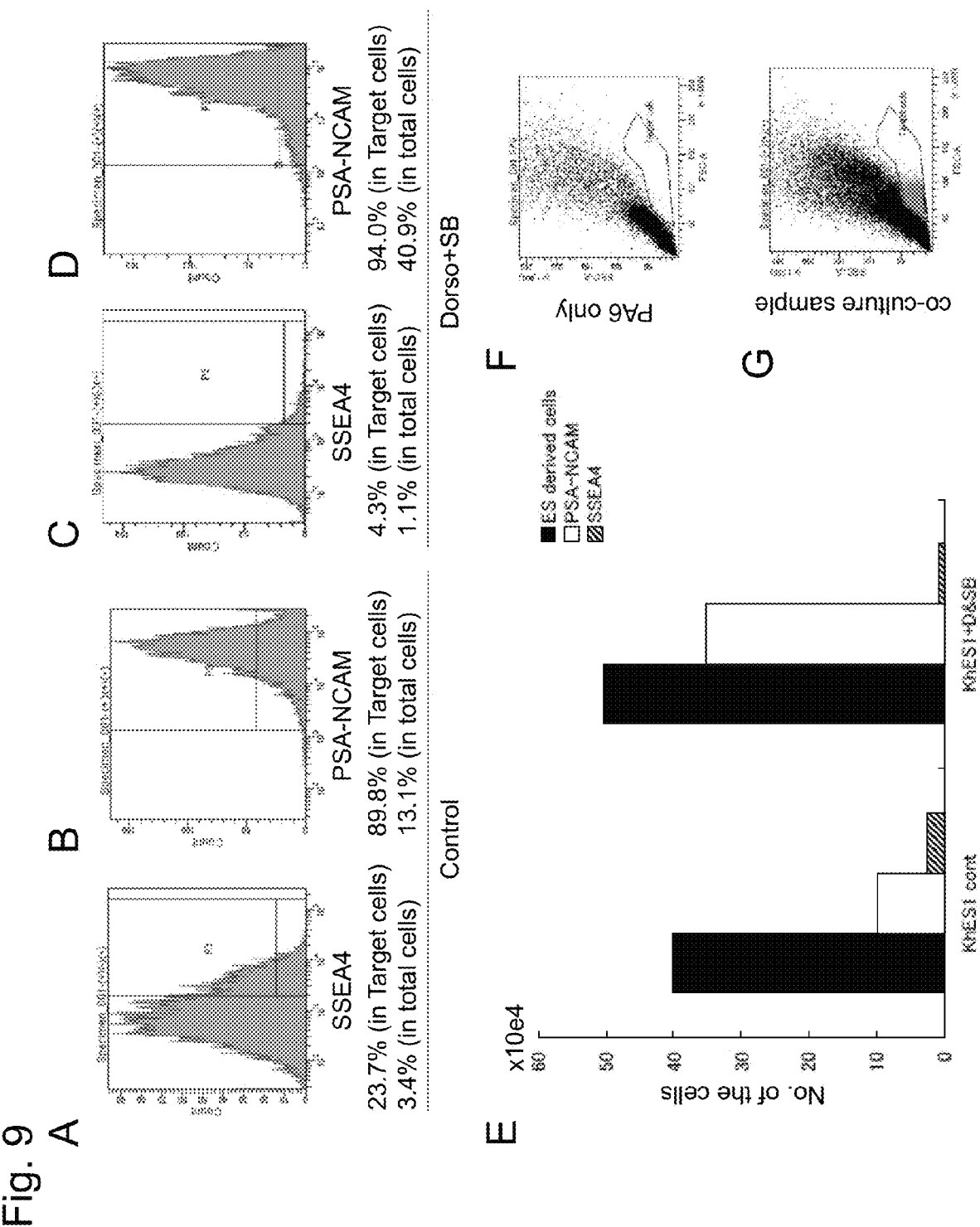
FIG. 9 shows FACS graphs showing distributions of SSEA4-expressing (or positive) cells (FIG. 9A and FIG. 9C) and PSA-NCAM-expressing cells (FIG. 9B and FIG. 9D) in control groups (FIG. 9A and FIG. 9B) prepared by inducing the differentiation of KhES1 only via culture on PA6 cells and in groups (FIG. 9C and FIG. 9D) prepared by inducing differentiation on PA6 cells through addition of Dorsomorphin and SB431542 to medium. Regarding values presented herein, the upper shows the rates (%) of cells expressing each marker in KhES1-derived cells ("in Target cells"), and the lower shows the rates (%) of cells expressing each marker in all cells existing within dishes containing KhES1-derived cells and PA6 cells ("in total cells").

Regarding the above result, the efficiency of induction into neural precursor cells was determined based on the number of colonies, each of which contained at least one cell positive for a marker gene. This is inappropriate for comparison of induction efficiency in a whole cell. Hence, for observation of differentiation induction based on the cell unit, but not based on the colony unit, FACS analysis was conducted. According to the conventional stromal cell-derived inducing activity method (SDIA method) (Kawasaki H, et al. Neuron. 28: 31-40, 2000 or Kawasaki H, et al. Proc Natl Acad Sci U.S.A. 99: 1580-5, 2002), differentiation was induced without using Dorsomorphin or SB431542, but using PA6 cells as feeder cells. On day 14 after differentiation induction, the cells were analyzed by FACS (FIG. 8). This method may result in some cell lines for which SSEA4 (an undifferentiation marker)-positive cells are observed. Accordingly, the method is not a reliable induction method because of differences in differentiation resistance among cell lines. Next, the differentiation of ES cells (KhES1) was induced by a method involving the addition of Dorsomorphin and SB431542. The number of PSA-NCAM-positive cells was 3 or more times greater than the number of the same in a control group to which nothing had been added, and the number of SSEA4-positive cells was found to decrease (FIG. 9). Therefore, it was confirmed that highly efficient differentiation into neural precursor cells is possible by the method of using Dorsomorphin and SB431542.

Example 2 iPS cells (G4) were subjected to formation of an embryoid body under low adhesion conditions, and Dorsomorphin and SB431542 were added to the cells, thereby differentiating the cells into the neural precursor cells. As a result, on day 14 after differentiation induction, almost 99.6% of cells were positive for PSA-NCAM (FIG. 10A). Also, as a result of immunostaining, cells subjected to differentiation induction were positive for Nestin and Pax6, the early stage neural markers (FIG. 10B). As described above, it was confirmed that, using the method for inducing differentiation in the absence of feeder cells, highly efficient differentiation into neural precursor cells was possible using Dorsomorphin and SB431542.

Example 3

Induction of differentiation into neural precursor cells using each drug (Matrigel method) iPS cells (G4) were cultured for 14 days by the Matrigel method under the following conditions: DMSO alone (control) (C group); Noggin alone (N group); Noggin+SB431542 (NS group); Dorsomorphin alone (D group); SB431542 alone (S group); Dorsomorphin+SB431542 (DS group); LDN-193189 (1 nM) (L1 group); LDN-193189 (5 nM) (L5 group); LDN-193189 (10 nM) (L10 group); LDN-193189 (5 nM)+SB431542 (L5S group); LDN-193189 (10 nM)+SB431542 (L10S group); LDN-193189 (50 nM)+SB431542 (L50S group); and LDN-193189 (100 nM)+SB431542 (L100S group). FIG. 11 and FIG. 12 show the results.

After differentiation induction, it was confirmed that there were a large number of viable cells in the NS group, the DS group, the L50S group, and the L100S group as a result of visually observing cells and determining the number of cells on day 14.

Subsequently, whether or not differentiation into neural precursor cells was possible was confirmed based on the expression of the neural cell marker PAX6 and the undifferentiation marker Nanog (FIG. 13). As a result, the number of PAX6-positive and Nanog-negative cells was high in the L100S group. Thus, it was confirmed that the induction of the differentiation into neural precursor cells under the aforementioned conditions was relatively satisfactory.

Example 4

Determination of an optimal concentration of LDN-193189 for differentiation into neural precursor cells (SDIA method)

Human ES cells (KhES-1, KhES-4, and KhES-5) were subjected to differentiation induction performed by a stromal cell-derived inducing activity method (SDIA method) using LDN-193189 at a concentration ranging from 5 nM to 1000 nM, in order to determine an optimal concentration of LDN-193189.

FIG. 14 shows staining images obtained using anti-Nestin antibody on day 14 after differentiation induction. Differentiation of Kh-ES5 cells was induced by adding SB431542 and LDN-193189 (at several concentrations) to the cells, so as to induce their differentiation into neural precursor cells. Therefore, it was confirmed that the differentiation of KhES-5 cells into neural precursor cells was induced relatively successfully when the concentration of LDN-193189 was 50 nM or higher (L50S group, L100S group, and L500nMS group). Also, it was not observed that the effect was increased when the concentration of LDN-193189 was higher than 50 nM.

Next, the KhES-1 cell line and the KhES-4 cell line were subjected to differentiation induction by adding LDN-193189 and SB431542. It was thus confirmed that Nestin-positive cells were relatively satisfactory when the concentration of LDN-193189 ranged from 25 nM to 75 nM (FIG. 15A). Similarly, the cells were stained with the Pax6 neural marker. It was confirmed that the cells were stained to the highest degree when the concentration of LDN-193189 was 20 nM (FIG. 15B).

Example 5

The neural cells inducing efficiency with 6 combinations of drugs was shown in FIG. 16. Each combination of drugs was not different from each other, but under the condition of pre-established DFK5% contained with Dorsomorphin and SB431542, the neural differentiation induction is lower effect than the others. On the other hand, the condition of GMK8% contained with LDN913189 and A-83-01 had higher probability of survival than that of the condition of DFK5% contained with Dorsomorphin and SB431542.

The various types of marker genes (Oct3/4, PSA-NCAM, Tuj-1, SSEA1 and SSEA4) of differentiated cells cultured in the condition of GMK8% contained with LDN913189 and A-83-01 were analyzed with flow cytometer (FIG. 17). Undifferentiated marker genes (Oct3/4 and SSEA4) were decrease and neural marker genes (PSA-NCAM, Tuj-1 and SSEA1) were increased. For these result, the culture condition was induced to effective neural differentiation.

INDUSTRIAL APPLICABILITY

According to the present invention, it becomes possible to efficiently produce neural precursor cells from pluripotent stem cells such as ES cells or iPS cells while decreasing a survival rate of undifferentiated cells. The neural precursor cells can be used in the field of regenerative medicine intended to treat diseases of the nervous system.

The invention claimed is:

1. A method for inducing differentiation of a pluripotent stem cell into a neural precursor cell, the method comprising:
   treating the pluripotent stem cell with a p160-Rho-associated coiled-coil kinase (ROCK) inhibitor; and
   culturing the treated pluripotent stem cell in a culture medium to induce the differentiation into the neural precursor cell in a culture medium that comprises 4-(6-(4-(piperazin-1-yl)phenyl)pyrazolo[1,5-a]pyrimidin-3-yl)quinolone (LDN-193189) and a TGFβ family inhibitor selected from the group consisting of 4-[4-(1,3-benzodioxol-5-yl)-5-(2-pyridinyl)-1H-imidazol-2-yl] benzamide (SB431542) and 3-(6-methylpyridin-2-yl)-1-phenylthiocarbamoyl-4-quinolin-4-ylpyrazole (A-83-01), wherein the concentration of LDN-193189 is 50 nM or higher.

2. The method of claim 1, wherein the culture medium further comprises a feeder cell, which is a stromal cell.

3. The method of claim 2, wherein the stromal cell is a mouse stromal cell.

4. The method of claim 1, wherein the culture medium is serum free and prior to the culturing of the differentiation induction an embryoid body is formed from the pluripotent stem cell.

5. The method of claim 1, wherein the culture is performed on a Matrigel™-coated dish without feeder cells.

6. The method of claim 1, wherein the pluripotent stem cell is an embryonic stem cell or an induced pluripotent stem cell.

7. The method of claim 1, wherein the TGFβ family inhibitor is 4-[4-(1,3-benzodioxol-5-yl)-5-(2-pyridinyl)-1H-imidazol-2-yl] benzamide (SB431542).

8. The method of claim 1, wherein the TGFβ family inhibitor is 3-(6-methylpyridin-2-yl)-1-phenylthiocarbamoyl-4-quinolin-4-ylpyrazole (A-83-01).

9. The method of claim 1, wherein the pluripotent stem cell is an embryonic stem cell.

10. The method of claim 1, wherein the pluripotent stem cell is an induced pluripotent stem cell.

11. The method according to claim 1, wherein the culturing is performed in the absence of feeder cells.

12. The method according to claim 1, wherein the culturing is performed for a period of from 7 days to 21 days.

13. The method according to claim 1, wherein the neural precursor cell is positive for PSA-NCAM, Nestin, and Pax6.

14. The method according to claim 1, wherein the neural precursor cell is positive for PSA-NCAM, TUJ1 and SSEA1 and negative for Oct3/4 and SSEA4.

15. A method for inducing differentiation of a pluripotent stem cell into a neural precursor cell in the presence of small molecule substances which have activity to differentiate a pluripotent stem cell into a neural precursor cell, wherein the method comprises:
   treating the pluripotent cell with a p160-Rho-associated coiled-coil kinase (ROCK) inhibitor; and
   culturing the treated pluripotent stem cell in a culture medium, in the absence of feeder cells, for a period of from 7 days to 21 days, wherein the culture medium comprises small molecule substances comprising 4-(6-(4-(piperazin-1-yl)phenyl)pyrazolo[1,5-a]pyrimidin-3-yl)quinolone (LDN-193189) and a TGFβ family inhibitor selected from the group consisting of 4-[4-(1,3-benzodioxol-5-yl)-5-(2-pyridinyl)-1H-imidazol-2-yl] benzamide (SB431542) and 3-(6-methylpyridin-2-yl)-1-phenylthiocarbamoyl-4-quinolin-4-ylpyrazole (A-83-01), wherein the concentration of LDN-193189 is 50 nM or higher, thereby to induce the differentiation into the neural precursor cell.

* * * * *